(12) United States Patent
Oron et al.

(10) Patent No.: US 10,105,540 B2
(45) Date of Patent: Oct. 23, 2018

(54) OPTIMIZATION OF APPLICATION OF CURRENT

(71) Applicant: BLUEWIND MEDICAL LTD., Herzlia (IL)

(72) Inventors: Gur Oron, Tel Aviv (IL); Bar Eytan, Gedera (IL); Eran Benjamin, Tel Aviv (IL); Anton Plotkin, Tel-Aviv (IL); Yossi Gross, Moshav Mazor (IL)

(73) Assignee: BLUEWIND MEDICAL LTD., Herzlia (IL)

( * ) Notice: Subject to any disclaimer, the term of this patent is extended or adjusted under 35 U.S.C. 154(b) by 0 days.

(21) Appl. No.: 14/935,941

(22) Filed: Nov. 9, 2015

(65) Prior Publication Data

US 2017/0128724 A1 May 11, 2017

(51) Int. Cl.
*A61N 1/36* (2006.01)
*A61N 1/05* (2006.01)
*A61N 1/372* (2006.01)

(52) U.S. Cl.
CPC ....... *A61N 1/36071* (2013.01); *A61N 1/0551* (2013.01); *A61N 1/36132* (2013.01);
(Continued)

(58) Field of Classification Search
CPC ....... A61N 1/36071; A61N 1/36132–1/36139; A61N 1/3605; A61N 1/36057; A61N 1/37247
See application file for complete search history.

(56) References Cited

U.S. PATENT DOCUMENTS

| 3,411,507 A | 11/1968 | Wingrove |
| 3,693,625 A | 9/1972 | Auphan |

(Continued)

FOREIGN PATENT DOCUMENTS

| DE | 102008054403 A1 | 6/2010 |
| EP | 0 688 577 | 12/1995 |

(Continued)

OTHER PUBLICATIONS

An Office Action dated Aug. 8, 2016, which issued during the prosecution of U.S. Appl. No. 14/735,741.

(Continued)

*Primary Examiner* — George Evanisko
(74) *Attorney, Agent, or Firm* — Sughrue Mion, PLLC

(57) ABSTRACT

Apparatus is provided, comprising: (a) an implantable excitation unit, configured to induce action potentials in a nerve of a subject by applying an excitatory current; (b) an implantable blocking unit, configured to block the induced action potentials from propagating along the nerve by applying a blocking current; and (c) an extracorporeal controller, comprising circuitry configured: (i) to wirelessly drive the excitation unit to apply the excitatory current, (ii) in a first mode, to wirelessly drive the blocking unit to apply the blocking current while not driving the excitation unit to apply the excitatory current, (iii) in a second mode, to wirelessly drive the blocking unit to apply the blocking current while driving the excitation unit to apply the excitatory current, and (iv) to wirelessly alter a parameter of the blocking current, based on sensing performed while the extracorporeal controller is in the second mode.

10 Claims, 12 Drawing Sheets

(52) U.S. Cl.
CPC ..... *A61N 1/36139* (2013.01); *A61N 1/37205* (2013.01); *A61N 1/37223* (2013.01); *A61N 1/37247* (2013.01); *A61N 1/37264* (2013.01)

(56) References Cited

U.S. PATENT DOCUMENTS

| | | | |
|---|---|---|---|
| 3,941,136 A | 3/1976 | Bucalo | |
| 4,019,518 A | 4/1977 | Maurer et al. | |
| 4,161,952 A | 7/1979 | Kinney et al. | |
| 4,338,945 A | 7/1982 | Kosugi et al. | |
| 4,392,496 A | 7/1983 | Stanton | |
| 4,535,785 A | 8/1985 | Van Den Honert | |
| 4,542,753 A | 9/1985 | Brenman et al. | |
| 4,559,948 A | 12/1985 | Liss et al. | |
| 4,573,481 A | 3/1986 | Bullara | |
| 4,585,005 A | 4/1986 | Lue et al. | |
| 4,602,624 A | 7/1986 | Naples | |
| 4,608,985 A | 9/1986 | Crish | |
| 4,628,942 A | 12/1986 | Sweeney | |
| 4,632,116 A | 12/1986 | Rosen | |
| 4,649,936 A | 3/1987 | Ungar | |
| 4,663,102 A | 5/1987 | Brenman et al. | |
| 4,702,254 A | 10/1987 | Zabara | |
| 4,739,764 A | 4/1988 | Lau | |
| 4,808,157 A | 2/1989 | Coombs | |
| 4,867,164 A | 9/1989 | Zabara | |
| 4,926,865 A | 5/1990 | Oman | |
| 4,962,751 A | 10/1990 | Krauter | |
| 5,025,807 A | 6/1991 | Zabara | |
| 5,042,497 A | 8/1991 | Shapland | |
| 5,058,599 A | 10/1991 | Andersen | |
| 5,069,680 A | 12/1991 | Grandjean | |
| 5,170,802 A | 12/1992 | Mehra | |
| 5,178,161 A | 1/1993 | Kovacs | |
| 5,188,104 A | 2/1993 | Wernicke | |
| 5,193,539 A | 3/1993 | Schulman et al. | |
| 5,193,540 A | 3/1993 | Schulman et al. | |
| 5,199,428 A | 4/1993 | Obel et al. | |
| 5,199,430 A | 4/1993 | Fang | |
| 5,203,326 A | 4/1993 | Collins | |
| 5,205,285 A | 4/1993 | Baker, Jr. | |
| 5,215,086 A | 6/1993 | Terry, Jr. | |
| 5,224,491 A | 7/1993 | Mehra | |
| 5,263,480 A | 11/1993 | Wernicke | |
| 5,282,468 A | 2/1994 | Klepinski | |
| 5,284,479 A | 2/1994 | De Jong | |
| 5,292,344 A | 3/1994 | Douglas | |
| 5,299,569 A | 4/1994 | Wernicke | |
| 5,312,439 A | 5/1994 | Loeb | |
| 5,314,495 A | 5/1994 | Kovacs | |
| 5,330,507 A | 7/1994 | Schwartz | |
| 5,335,657 A | 8/1994 | Terry, Jr. | |
| 5,411,531 A | 5/1995 | Hill et al. | |
| 5,411,535 A | 5/1995 | Fujii et al. | |
| 5,423,872 A | 6/1995 | Cigaina | |
| 5,437,285 A | 8/1995 | Verrier et al. | |
| 5,439,938 A | 8/1995 | Synder et al. | |
| 5,454,840 A | 10/1995 | Krakovsky et al. | |
| 5,487,760 A | 1/1996 | Villafana | |
| 5,505,201 A | 4/1996 | Grill, Jr. | |
| 5,507,784 A | 4/1996 | Hill et al. | |
| 5,540,730 A | 7/1996 | Terry, Jr. | |
| 5,540,733 A | 7/1996 | Testerman et al. | |
| 5,540,734 A | 7/1996 | Zabara | |
| 5,549,655 A | 8/1996 | Erickson | |
| 5,562,718 A | 10/1996 | Palermo | |
| 5,571,118 A | 11/1996 | Boutos | |
| 5,571,150 A | 11/1996 | Wernicke | |
| 5,578,061 A | 11/1996 | Stroetmann et al. | |
| 5,591,216 A | 1/1997 | Testerman et al. | |
| 5,615,684 A | 4/1997 | Hagel et al. | |
| 5,634,462 A | 6/1997 | Tyler et al. | |
| 5,645,570 A | 7/1997 | Corbucci | |
| 5,690,681 A | 11/1997 | Geddes et al. | |
| 5,690,691 A | 11/1997 | Chen | |
| 5,700,282 A | 12/1997 | Zabara | |
| 5,707,400 A | 1/1998 | Terry, Jr. | |
| 5,711,316 A | 1/1998 | Elsberry et al. | |
| 5,716,385 A | 2/1998 | Mittal | |
| 5,748,845 A | 5/1998 | Labun et al. | |
| 5,755,750 A | 5/1998 | Petruska | |
| 5,775,331 A | 7/1998 | Raymond et al. | |
| 5,776,170 A | 7/1998 | Macdonald et al. | |
| 5,776,171 A | 7/1998 | Peckham | |
| 5,814,089 A | 9/1998 | Stokes | |
| 5,824,027 A | 10/1998 | Hoffer et al. | |
| 5,832,932 A | 11/1998 | Elsberry et al. | |
| 5,833,709 A | 11/1998 | Rise et al. | |
| 5,836,994 A | 11/1998 | Bourgeois | |
| 5,861,019 A | 1/1999 | Sun et al. | |
| 5,916,239 A | 6/1999 | Geddes et al. | |
| 5,938,584 A | 8/1999 | Ardito et al. | |
| 5,944,680 A | 8/1999 | Christopherson | |
| 5,954,758 A | 9/1999 | Peckham | |
| 5,991,664 A | 11/1999 | Seligman | |
| 6,002,964 A | 12/1999 | Feler et al. | |
| 6,026,326 A | 2/2000 | Bardy | |
| 6,026,328 A | 2/2000 | Peckham | |
| 6,032,076 A | 2/2000 | Melvin et al. | |
| 6,051,017 A | 4/2000 | Loeb et al. | |
| 6,058,328 A | 5/2000 | Levine et al. | |
| 6,058,331 A | 5/2000 | King et al. | |
| 6,061,596 A | 5/2000 | Richmond et al. | |
| 6,066,163 A | 5/2000 | John | |
| 6,071,274 A | 6/2000 | Thompson et al. | |
| 6,073,048 A | 6/2000 | Kieval et al. | |
| 6,091,992 A | 6/2000 | Bourgeois | |
| 6,083,249 A | 7/2000 | Familoni | |
| 6,086,525 A | 7/2000 | Davey et al. | |
| 6,091,922 A | 7/2000 | Bisaiji | |
| 6,091,977 A | 7/2000 | Tarjan et al. | |
| 6,094,598 A | 7/2000 | Elsberry et al. | |
| 6,097,984 A | 8/2000 | Douglas | |
| 6,104,955 A | 8/2000 | Bourgeois | |
| 6,104,956 A | 8/2000 | Naritoku et al. | |
| 6,104,960 A | 8/2000 | Duysens et al. | |
| 6,119,516 A | 9/2000 | Hock | |
| 6,146,335 A | 11/2000 | Gozani | |
| 6,148,232 A | 11/2000 | Avrahami | |
| 6,161,029 A | 12/2000 | Spreigl et al. | |
| 6,161,048 A | 12/2000 | Sluijter et al. | |
| 6,167,304 A | 12/2000 | Loos | |
| 6,169,924 B1 | 1/2001 | Meloy et al. | |
| 6,205,359 B1 | 3/2001 | Boveja | |
| 6,212,435 B1 | 4/2001 | Lattner et al. | |
| 6,214,032 B1 | 4/2001 | Loeb et al. | |
| 6,230,061 B1 | 5/2001 | Hartung | |
| 6,240,314 B1 | 5/2001 | Plicchi et al. | |
| 6,240,316 B1 | 5/2001 | Richmond | |
| 6,246,912 B1 | 6/2001 | Sluijter et al. | |
| 6,266,564 B1 | 7/2001 | Schwartz | |
| 6,272,377 B1 | 8/2001 | Sweeney et al. | |
| 6,272,383 B1 | 8/2001 | Grey | |
| 6,292,703 B1 | 9/2001 | Meier et al. | |
| 6,319,241 B1 | 11/2001 | King | |
| 6,332,089 B1 | 12/2001 | Acker | |
| 6,341,236 B1 | 1/2002 | Osorio et al. | |
| 6,345,202 B2 | 2/2002 | Richmond et al. | |
| 6,356,784 B1 | 3/2002 | Lozano et al. | |
| 6,356,788 B2 | 3/2002 | Boveja | |
| 6,366,813 B1 | 4/2002 | Dilorenzo | |
| 6,381,499 B1 | 4/2002 | Taylor et al. | |
| 6,400,982 B2 | 6/2002 | Sweeney et al. | |
| 6,405,079 B1 | 6/2002 | Ansarinia | |
| 6,415,178 B1 | 7/2002 | Ben-Haim et al. | |
| 6,442,432 B2 | 8/2002 | Lee | |
| 6,445,953 B1 | 9/2002 | Bulkes et al. | |
| 6,449,507 B1 | 9/2002 | Hill et al. | |
| 6,456,878 B1 | 9/2002 | Yerich et al. | |
| 6,463,328 B1 | 10/2002 | John | |
| 6,473,644 B1 | 10/2002 | Terry, Jr. et al. | |
| 6,493,585 B2 | 12/2002 | Plicchi et al. | |
| 6,496,729 B2 | 12/2002 | Thompson | |
| 6,496,730 B1 | 12/2002 | Kleckner et al. | |

(56) References Cited

U.S. PATENT DOCUMENTS

| | | |
|---|---|---|
| 6,522,926 B1 | 2/2003 | Kieval et al. |
| 6,542,774 B2 | 4/2003 | Hill et al. |
| 6,564,096 B2 | 5/2003 | Mest |
| 6,571,122 B2 | 5/2003 | Schroeppel et al. |
| 6,582,441 B1 | 6/2003 | He et al. |
| 6,587,727 B2 | 7/2003 | Osorio et al. |
| 6,600,954 B2 | 7/2003 | Cohen |
| 6,600,956 B2 | 7/2003 | Maschino et al. |
| 6,606,521 B2 | 8/2003 | Paspa et al. |
| 6,610,713 B2 | 8/2003 | Tracey |
| 6,618,627 B2 | 9/2003 | Lattner et al. |
| 6,622,041 B2 | 9/2003 | Terry, Jr. et al. |
| 6,628,987 B1 | 9/2003 | Hill et al. |
| 6,641,542 B2 | 11/2003 | Cho et al. |
| 6,650,943 B1 | 11/2003 | Whitehurst et al. |
| 6,658,297 B2 | 12/2003 | Loeb |
| 6,668,191 B1 | 12/2003 | Boveja |
| 6,671,556 B2 | 12/2003 | Osorio et al. |
| 6,682,480 B1 | 1/2004 | Habib et al. |
| 6,684,105 B2 | 1/2004 | Cohen et al. |
| 6,690,971 B2 | 2/2004 | Schauerte et al. |
| 6,733,485 B1 | 5/2004 | Whitehurst et al. |
| 6,735,474 B1 | 5/2004 | Loeb et al. |
| 6,770,022 B2 | 8/2004 | Mechlenburg |
| 6,829,508 B2 | 12/2004 | Schulman |
| 6,839,594 B2 | 1/2005 | Cohen |
| 6,862,479 B1 | 3/2005 | Whitehurst et al. |
| 6,892,098 B2 | 5/2005 | Ayal |
| 6,907,295 B2 | 6/2005 | Gross et al. |
| 6,909,917 B2 | 6/2005 | Woods et al. |
| 7,025,730 B2 | 4/2006 | Cho et al. |
| 7,027,860 B2 | 4/2006 | Bruninga et al. |
| 7,047,076 B1 | 5/2006 | Li et al. |
| 7,054,692 B1 | 5/2006 | Whitehurst et al. |
| 7,149,575 B2 | 12/2006 | Ostroff et al. |
| 7,177,698 B2 | 2/2007 | Klosterman et al. |
| 7,190,998 B2 | 3/2007 | Shalev et al. |
| 7,212,867 B2 | 5/2007 | Venrooij et al. |
| 7,228,178 B2 | 6/2007 | Carroll |
| 7,263,405 B2 | 8/2007 | Boveja et al. |
| 7,277,749 B2 | 10/2007 | Gordon et al. |
| 7,289,853 B1 | 10/2007 | Campbell et al. |
| 7,324,852 B2 | 1/2008 | Barolat et al. |
| 7,324,853 B2 | 1/2008 | Ayal |
| 7,389,145 B2 | 6/2008 | Kilgore et al. |
| 7,483,752 B2 | 1/2009 | Von arx et al. |
| 7,489,969 B2 | 2/2009 | Knudson et al. |
| 7,502,652 B2 | 3/2009 | Gaunt et al. |
| 7,532,932 B2 | 5/2009 | Denker et al. |
| 7,536,226 B2 | 5/2009 | Williams |
| 7,628,750 B2 | 12/2009 | Cohen |
| 7,630,771 B2 | 12/2009 | Cauller |
| 7,634,313 B1 | 12/2009 | Kroll et al. |
| 7,655,014 B2 | 2/2010 | Ko et al. |
| 7,657,311 B2 | 2/2010 | Bardy et al. |
| 7,657,322 B2 | 2/2010 | Bardy et al. |
| 7,660,632 B2 | 2/2010 | Kirby et al. |
| 7,680,538 B2 | 3/2010 | Durand et al. |
| 7,711,434 B2 | 5/2010 | Denker et al. |
| 7,734,355 B2 | 6/2010 | Cohen et al. |
| 7,736,379 B2 | 6/2010 | Ewers et al. |
| 7,778,703 B2 | 8/2010 | Gross et al. |
| 7,780,625 B2 | 8/2010 | Bardy |
| 7,797,050 B2 | 9/2010 | Libbus et al. |
| 7,848,818 B2 | 12/2010 | Barolat et al. |
| 7,885,709 B2 | 2/2011 | Ben-David |
| 7,890,185 B2 | 2/2011 | Cohen et al. |
| 7,917,226 B2 | 5/2011 | Nghiem |
| 7,937,148 B2 | 5/2011 | Jacobson |
| 7,941,218 B2 | 5/2011 | Sambelashvili et al. |
| 7,974,706 B2 | 7/2011 | Moffitt et al. |
| 7,991,467 B2 | 8/2011 | Markowitz et al. |
| 7,996,089 B2 | 8/2011 | Haugland et al. |
| 7,996,092 B2 | 8/2011 | Mrva et al. |
| 8,019,443 B2 | 9/2011 | Scheicher et al. |
| 8,046,085 B2 | 10/2011 | Knudson et al. |
| 8,055,350 B2 | 11/2011 | Roberts |
| 8,075,556 B2 | 12/2011 | Betts |
| 8,090,438 B2 | 1/2012 | Bardy et al. |
| 8,115,448 B2 | 2/2012 | John |
| 8,131,377 B2 | 3/2012 | Shhi et al. |
| 8,170,675 B2 | 5/2012 | Alataris et al. |
| 8,177,792 B2 | 5/2012 | Lubock et al. |
| 8,185,207 B2 | 5/2012 | Molnar et al. |
| 8,209,021 B2 | 6/2012 | Alataris et al. |
| 8,224,453 B2 | 7/2012 | De Ridder |
| 8,255,057 B2 | 8/2012 | Fang et al. |
| 8,355,792 B2 | 1/2013 | Alataris et al. |
| 8,359,102 B2 | 1/2013 | Alataris et al. |
| 8,359,103 B2 | 1/2013 | Alataris et al. |
| 8,396,559 B2 | 3/2013 | Alataris et al. |
| 8,428,748 B2 | 4/2013 | Alataris et al. |
| 8,463,404 B2 | 6/2013 | Levi et al. |
| 8,509,905 B2 | 8/2013 | Alataris et al. |
| 8,509,906 B2 | 8/2013 | Walker et al. |
| 8,554,326 B2 | 10/2013 | Alataris et al. |
| 8,634,927 B2 | 1/2014 | Olson et al. |
| 8,649,874 B2 | 2/2014 | Alataris et al. |
| 8,694,108 B2 | 4/2014 | Alataris et al. |
| 8,694,109 B2 | 4/2014 | Alataris et al. |
| 8,712,533 B2 | 4/2014 | Alataris et al. |
| 8,718,781 B2 | 5/2014 | Alataris et al. |
| 8,718,782 B2 | 5/2014 | Alataris et al. |
| 8,755,893 B2 | 6/2014 | Gross et al. |
| 8,768,472 B2 | 7/2014 | Fang et al. |
| 8,774,926 B2 | 7/2014 | Alataris et al. |
| 8,788,045 B2 | 7/2014 | Gross et al. |
| 8,792,988 B2 | 7/2014 | Alataris et al. |
| 8,849,410 B2 | 9/2014 | Walker et al. |
| 8,862,239 B2 | 10/2014 | Alataris et al. |
| 8,868,192 B2 | 10/2014 | Alataris et al. |
| 8,874,217 B2 | 10/2014 | Alataris et al. |
| 8,874,221 B2 | 10/2014 | Alataris et al. |
| 8,874,222 B2 | 10/2014 | Alataris et al. |
| 8,880,177 B2 | 11/2014 | Alataris et al. |
| 8,886,326 B2 | 11/2014 | Alataris et al. |
| 8,886,327 B2 | 11/2014 | Alataris et al. |
| 8,886,328 B2 | 11/2014 | Alataris et al. |
| 8,892,209 B2 | 11/2014 | Alataris et al. |
| 9,248,279 B2 * | 2/2016 | Chen .................. A61N 1/05 |
| 2001/0003799 A1 | 6/2001 | Boveja |
| 2002/0035335 A1 | 3/2002 | Schauerte |
| 2002/0055761 A1 | 5/2002 | Mann et al. |
| 2002/0077554 A1 | 6/2002 | Schwartz et al. |
| 2002/0099419 A1 | 7/2002 | Cohen et al. |
| 2002/0107553 A1 | 8/2002 | Hill et al. |
| 2002/0124848 A1 | 9/2002 | Sullivan et al. |
| 2002/0183805 A1 | 12/2002 | Fang et al. |
| 2002/0183817 A1 | 12/2002 | Van Venrooij et al. |
| 2003/0018365 A1 | 1/2003 | Loeb |
| 2003/0040774 A1 | 2/2003 | Terry et al. |
| 2003/0060858 A1 | 3/2003 | Kieval et al. |
| 2003/0100933 A1 * | 5/2003 | Ayal .................. A61N 1/36003 607/48 |
| 2003/0114905 A1 | 6/2003 | Kuzma |
| 2003/0176898 A1 | 9/2003 | Gross et al. |
| 2003/0216775 A1 | 11/2003 | Hill et al. |
| 2003/0229380 A1 | 12/2003 | Adams et al. |
| 2003/0233129 A1 | 12/2003 | Matos |
| 2003/0236557 A1 | 12/2003 | Whitehurst et al. |
| 2003/0236558 A1 * | 12/2003 | Whitehurst .......... A61N 1/0556 607/45 |
| 2004/0015204 A1 | 1/2004 | Whitehurst et al. |
| 2004/0015205 A1 * | 1/2004 | Whitehurst ........ A61N 1/37205 607/48 |
| 2004/0019368 A1 | 1/2004 | Lattner et al. |
| 2004/0048795 A1 | 3/2004 | Ivanova et al. |
| 2004/0059392 A1 | 3/2004 | Parramon et al. |
| 2004/0073270 A1 | 4/2004 | Firlik et al. |
| 2004/0254624 A1 | 6/2004 | Johnson |
| 2004/0138721 A1 | 7/2004 | Osorio et al. |
| 2004/0152958 A1 | 8/2004 | Frei et al. |
| 2004/0158119 A1 | 8/2004 | Osorio et al. |
| 2004/0167584 A1 | 8/2004 | Carroll et al. |

(56) References Cited

U.S. PATENT DOCUMENTS

| | | |
|---|---|---|
| 2004/0215289 A1 | 10/2004 | Fukui |
| 2004/0249416 A1 | 12/2004 | Yun et al. |
| 2004/0249431 A1 | 12/2004 | Ransbury et al. |
| 2004/0254612 A1* | 12/2004 | Ezra ............. A61N 1/36114 607/5 |
| 2005/0113894 A1 | 5/2005 | Zilberman et al. |
| 2005/0131467 A1 | 6/2005 | Boveja |
| 2005/0131495 A1 | 6/2005 | Parramon et al. |
| 2005/0143789 A1 | 6/2005 | Whitehurst |
| 2005/0165457 A1 | 7/2005 | Benser et al. |
| 2005/0222644 A1 | 10/2005 | Killian et al. |
| 2006/0015153 A1 | 1/2006 | Gliner et al. |
| 2006/0074450 A1 | 4/2006 | Boveja et al. |
| 2006/0085039 A1 | 4/2006 | Hastings et al. |
| 2006/0100668 A1 | 5/2006 | Ben-David et al. |
| 2006/0129205 A1 | 6/2006 | Boveja et al. |
| 2006/0155345 A1 | 7/2006 | Williams et al. |
| 2006/0271137 A1 | 11/2006 | Stanton-Hicks |
| 2007/0032827 A1 | 2/2007 | Katims |
| 2007/0067000 A1 | 3/2007 | Strother et al. |
| 2007/0067007 A1 | 3/2007 | Schulman |
| 2007/0073354 A1 | 3/2007 | Knudson et al. |
| 2007/0083240 A1 | 4/2007 | Peterson et al. |
| 2007/0173893 A1 | 7/2007 | Pitts |
| 2007/0208392 A1 | 9/2007 | Kuschner et al. |
| 2007/0255369 A1 | 11/2007 | Bonde et al. |
| 2007/0293912 A1 | 12/2007 | Cowan et al. |
| 2008/0009914 A1 | 1/2008 | Buysman et al. |
| 2008/0021336 A1 | 1/2008 | Dobak |
| 2008/0027513 A1 | 1/2008 | Carbunaru |
| 2008/0039915 A1 | 2/2008 | Van Den Biggelaar |
| 2008/0103407 A1 | 5/2008 | Bolea et al. |
| 2008/0103572 A1 | 5/2008 | Gerber |
| 2008/0119898 A1 | 5/2008 | Ben-David et al. |
| 2008/0119911 A1 | 5/2008 | Rosero |
| 2008/0132964 A1 | 6/2008 | Cohen et al. |
| 2008/0269740 A1 | 10/2008 | Bonde et al. |
| 2009/0012590 A1 | 1/2009 | Inman et al. |
| 2009/0036975 A1 | 2/2009 | Ward et al. |
| 2009/0048642 A1 | 2/2009 | Goroszeniuk |
| 2009/0149912 A1 | 6/2009 | Dacey et al. |
| 2009/0152954 A1 | 6/2009 | Le et al. |
| 2009/0204170 A1 | 8/2009 | Hastings et al. |
| 2009/0204173 A1 | 8/2009 | Fang et al. |
| 2009/0270951 A1 | 10/2009 | Kallmyer |
| 2009/0281594 A1 | 11/2009 | King et al. |
| 2009/0326602 A1 | 12/2009 | Glukhovsky et al. |
| 2010/0016911 A1 | 1/2010 | Willis et al. |
| 2010/0094367 A1 | 4/2010 | Sen |
| 2010/0121405 A1 | 5/2010 | Ternes et al. |
| 2010/0125310 A1 | 5/2010 | Wilson et al. |
| 2010/0125313 A1 | 5/2010 | Lee et al. |
| 2010/0198298 A1 | 8/2010 | Glukovsky et al. |
| 2010/0211131 A1 | 8/2010 | Williams et al. |
| 2010/0241195 A1 | 9/2010 | Meadows et al. |
| 2010/0249875 A1 | 9/2010 | Kishawi et al. |
| 2010/0312320 A1 | 9/2010 | Faltys et al. |
| 2010/0280568 A1 | 11/2010 | Bulkes et al. |
| 2010/0305392 A1 | 12/2010 | Gross et al. |
| 2010/0324630 A1 | 12/2010 | Lee et al. |
| 2011/0034782 A1 | 2/2011 | Sugimachi et al. |
| 2011/0046696 A1 | 2/2011 | Barolat et al. |
| 2011/0087337 A1 | 4/2011 | Forsell |
| 2011/0093036 A1 | 4/2011 | Mashiach |
| 2011/0137365 A1 | 6/2011 | Ben-Erza et al. |
| 2011/0152965 A1 | 6/2011 | Mashiach |
| 2011/0160792 A1 | 6/2011 | Fishel |
| 2011/0160793 A1 | 6/2011 | Gindele |
| 2011/0160798 A1 | 6/2011 | Ackermann et al. |
| 2011/0208260 A1 | 8/2011 | Jacobson |
| 2011/0208271 A1 | 8/2011 | Dobak |
| 2011/0224744 A1 | 9/2011 | Moffitt et al. |
| 2011/0230922 A1 | 9/2011 | Fishel |
| 2011/0251660 A1 | 10/2011 | Griswold |
| 2011/0270339 A1 | 11/2011 | Murray, III et al. |
| 2011/0282412 A1 | 11/2011 | Glukhovsky et al. |
| 2011/0301670 A1 | 12/2011 | Gross et al. |
| 2012/0010694 A1 | 1/2012 | Lutter et al. |
| 2012/0035679 A1 | 2/2012 | Dagan et al. |
| 2012/0041511 A1 | 2/2012 | Lee |
| 2012/0041514 A1 | 2/2012 | Gross et al. |
| 2012/0065701 A1 | 3/2012 | Cauller |
| 2012/0083857 A1 | 4/2012 | Bradley et al. |
| 2012/0101326 A1 | 4/2012 | Simon et al. |
| 2012/0123498 A1 | 5/2012 | Gross |
| 2012/0130448 A1 | 5/2012 | Woods et al. |
| 2012/0130463 A1 | 5/2012 | Ben-David et al. |
| 2012/0158081 A1 | 6/2012 | Gross et al. |
| 2012/0296389 A1 | 11/2012 | Fang et al. |
| 2013/0006326 A1 | 1/2013 | Ackermann et al. |
| 2013/0066393 A1 | 3/2013 | Gross et al. |
| 2013/0325081 A1 | 12/2013 | Karst et al. |
| 2013/0325084 A1* | 12/2013 | Lee ................. A61N 1/36071 607/46 |
| 2014/0214134 A1 | 7/2014 | Peterson |
| 2014/0296940 A1* | 10/2014 | Gross ............. A61N 1/36135 607/62 |
| 2015/0004709 A1 | 1/2015 | Nazarpoor |
| 2015/0018728 A1 | 1/2015 | Gross et al. |
| 2015/0039046 A1 | 2/2015 | Gross |
| 2015/0080979 A1 | 3/2015 | Lasko et al. |
| 2015/0100109 A1 | 4/2015 | Feldman et al. |
| 2015/0148861 A1 | 5/2015 | Gross |
| 2015/0258339 A1 | 9/2015 | Burchiel et al. |
| 2015/0335882 A1 | 11/2015 | Gross et al. |
| 2016/0206882 A1 | 7/2016 | Oron et al. |
| 2016/0206889 A1 | 7/2016 | Plotkin et al. |
| 2016/0206890 A1 | 7/2016 | Oron et al. |
| 2016/0361544 A1 | 12/2016 | Oron et al. |
| 2017/0119435 A1 | 5/2017 | Gross et al. |

FOREIGN PATENT DOCUMENTS

| | | |
|---|---|---|
| EP | 0831954 | 4/1998 |
| EP | 1533000 | 5/2005 |
| WO | 1998/010832 | 3/1998 |
| WO | 1998/037926 | 9/1998 |
| WO | 1998/043700 | 10/1998 |
| WO | 1998/043701 | 10/1998 |
| WO | 1999/026530 | 6/1999 |
| WO | 01/10432 | 2/2001 |
| WO | 2001/010375 | 2/2001 |
| WO | 01/26729 | 4/2001 |
| WO | 02/09808 | 2/2002 |
| WO | 2002/058782 | 8/2002 |
| WO | 2004/064729 | 8/2004 |
| WO | 2006/102370 | 9/2006 |
| WO | 2006/102626 | 9/2006 |
| WO | 2007/019491 | 2/2007 |
| WO | 2009/055574 | 4/2009 |
| WO | 2009/110935 | 9/2009 |
| WO | 2011/154937 | 12/2011 |
| WO | 2012/012591 | 1/2012 |
| WO | 2013/035092 | 3/2013 |
| WO | 2013/106884 A1 | 7/2013 |
| WO | 2013/111137 | 8/2013 |
| WO | 2013/156038 A1 | 10/2013 |
| WO | 2013/164829 | 11/2013 |
| WO | 2014/068577 A2 | 5/2014 |
| WO | 2014/068577 A3 | 5/2014 |
| WO | 2014/081978 | 5/2014 |
| WO | 2014/087337 | 6/2014 |
| WO | 2014/167568 | 10/2014 |
| WO | 2015/004673 | 1/2015 |
| WO | 2016/172109 A1 | 10/2016 |

OTHER PUBLICATIONS

Kucklick, Theodore R., ed. The medical device R&D handbook. Chapter 3—Intro to needles and cannulae. CRC Press, 2012.

An Office Action dated Dec. 12, 2016, which issued during the prosecution of U.S. Appl. No. 14/939,418.

(56) References Cited

OTHER PUBLICATIONS

An Office Action dated Nov. 21, 2016, which issued during the prosecution of U.S. Appl. No. 14/601,626.
Communication dated Feb. 3, 2017, issued from the Europe Patent Office in counterpart Application No. 16196878.9.
Communication dated Mar. 10, 2017, issued from the Europe Patent Office in counterpart Application No. 16196864.9.
An Office Action dated Feb. 27, 2017, which issued during the prosecution of U.S. Appl. No. 14/649,873.
C. de Balthasar, G. Cosendai, M. Hansen, D. Canfield, L. Chu, R. Davis, and J. Schulman, "Attachment of leads to RF-BION® microstimulators." Jul. 2005.
D.W. Eisele, A.R. Schwartz, and P.L. Smith, "Tongue neuromuscular and direct hypoglossal nerve stimulation for obstructive sleep apnea.," Otolaryngologic clinics of North America, vol. 36, 2003, p. 501.
G.E. Loeb, F.J.R. Richmond, J. Singh, R.A. Peck, W. Tan, Q. Zou, and N. Sachs, "RF-powered BIONs™ for stimulation and sensing," Engineering in Medicine and Biology Society, 2004. IEMBS'04. 26th Annual International Conference of the IEEE, 2005, pp. 4182-4185.
G.E. Loeb, F.J. Richmond, and L.L. Baker, "The BION devices: injectable interfaces with peripheral nerves and muscles," Neurosurgical focus, vol. 20, 2006, pp. 1-9.
E.A. Mann, T. Burnett, S. Cornell, and C.L. Ludlow, "The effect of neuromuscular stimulation of the genioglossus on the hypopharyngeal airway," The Laryngoscope, vol. 112, 2002, pp. 351-356.
A. Oliven, R.P. Schnall, G. Pillar, N. Gavriely, and M. Odeh, "Sublingual electrical stimulation of the tongue during wakefulness and sleep," Respiration physiology, vol. 127, 2001, pp. 217-226.
A. Oliven, D.J. O'Hearn, A. Boudewyns, M. Odeh, W. De Backer, P. van de Heyning, P.L. Smith, D.W. Eisele, L. Allan, H. Schneider, and others, "Upper airway response to electrical stimulation of the genioglossus in obstructive sleep apnea," Journal of Applied Physiology, vol. 95, 2003, p. 2023.
A. Oliven, M. Odeh, L. Geitini, R. Oliven, U. Steinfeld, A.R. Schwartz, and N. Tov, "Effect of coactivation of tongue protrusor and retractor muscles on pharyngeal lumen and airflow in sleep apnea patients," Journal of Applied Physiology, vol. 103, 2007, p. 1662.
A.R. Schwartz, D.W. Eisele, A. Hari, R. Testerman, D. Erickson, and P.L. Smith, "Electrical stimulation of the lingual musculature in obstructive sleep apnea," Journal of Applied Physiology, vol. 81, 1996, p. 643.
W.H. Tran, G.E. Loeb, F.J.R. Richmond, A.C. Dupont, K.C. Mahutte, C.S.H. Sassoon, and M.J. Dickel, "Development of asynchronous, intralingual electrical stimulation to treat obstructive sleep apnea," Engineering in Medicine and Biology Society, 2003. Proceedings of the 25th Annual International Conference of the IEEE, 2004, pp. 375-378.
W.H. Tran, G.E. Loeb, F.J.R. Richmond, R. Ahmed, G.T. Clark, and P.B. Haberman, "First subject evaluated with simulated BION™ treatment in genioglossus to prevent obstructive sleep apnea," Engineering in Medicine and Biology Society, 2004. IEMBS'04. 26th Annual International Conference of the IEEE, 2005, pp. 4287-4289.
P.R. Troyk, "Injectable electronic identification, monitoring, and stimulation systems," Biomedical Engineering, vol. 1, 1999, p. 177.
T.K. Whitehurst, J.H. Schulman, K.N. Jaax, and R. Carbunaru, "The Bion® Microstimulator and its Clinical Applications," Implantable Neural Prostheses 1, 2009, pp. 253-273.
D.J. Young, "Wireless powering and data telemetry for biomedical implants," Engineering in Medicine and Biology Society, 2009. EMBC 2009. Annual International Conference of the IEEE, 2009, pp. 3221-3224.
Reid R. Harrison, et al., "Wireless Neural Recording with Single Low-Power Integrated Circuit", IEEE Trans Neural Syst Rehabil Eng. Aug. 2009; 17(4): 322-329.

An International Search Report and a Written Opinion both dated Apr. 17, 2012 which issued during the prosecution of Applicant's PCT/IL11/00870.
Patents Galore: Implantable Neurostimulators Fight Snoring and Corpse Eye-Proof Scanners. Printout from http://medgadget.com/2006/03/patents_galore.html (Downloaded Jan. 2012).
Chris Seper, "Neuros Medical Launches to Develop New Device to Block Amputee, Chronic Pain", Mar. 16, 2009.
Urgent® PC, Simple. Safe. Effective. Neuromodulation System, Uroplasty, Mar. 2009.
"JumpStart and Case Technology Ventures Invest in Neuros Medical", CTV Case Technology Ventures, Mar. 17, 2009.
"Responses to median and tibial nerve stimulation in patients with chronic neuropathic pain", by Theuvenet, Brain Topography, vol. 11, No. 4, 1999, pp. 305-313(9)—an abstract.
Armstrong, J, "Is electrical stimulation effective in reducing neuropathic pain in patients with diabetes?", by Foot Ankle Surg. Jul.-Aug. 1997; 36(4): 260-3—an abstract.
Ross Davis, Cerebellar Stimulation for Cerebral Palsy Spasticity, Function and Seizures. Clinical Neuroscience Center, 1999. pp. 290-299.
An Office Action dated Feb. 13, 2004, which issued during the prosecution of U.S. Appl. No. 10/254,024.
Bathien et al., Inhibition and synchronisation of tremor induced by a muscle twitch. J. Neurol, Neurosurg. and Psych. 1980, 43, 713-718.
Mones and Weiss, The response of the tremor of patients with Parkinsonism to peripheral nerve stimulation. J. Neurol. Neurosurg. Psychiat. 1969, 32. 512-519.
Y. Zhang, et al., "Optimal Ventricular Rate Slowing During Atrial Fibrillation by Feedback AV Nodal-Selective Vagal Stimulation", Am J Physiol Heart Circ Physiol 282:H1102-H1110, 2002.
N.J.M Rijkhoff, et al., "Selective Stimulation of Small Diameter Nerve Fibers in a Mixed Bundle", Proceedings of the Annual Project Meeting Sensations/Neuros and Mid Term Review Meeting Neuros, Apr. 21-23, 1999.
M. Manfredi, "Differential Block of conduction of larger fibers in peripheral nerve by direct current", Arch. Ital. Biol. 108:52-71, 1970.
A Restriction Requirement dated May 11, 2012, which issued during the prosecution of U.S. Appl. No. 12/946,246.
Cerebral Palsy, Barry S. Russman MD, CCurrent Science Inc. 2000.
A Notice of Allowance dated Mar. 7, 2005, which issued during the prosecution of U.S. Appl. No. 10/254,024.
A Notice of Allowance dated Aug. 26, 2004, which issued during the prosecution of U.S. Appl. No. 10/254,024.
An Office Action dated Jun. 24, 2011, which issued during the prosecution of U.S. Appl. No. 12/796,102.
An International Search Report and a Written Opinion both dated Nov. 14, 2011, which issued during the prosecution of Applicant's PCT/IL2011/000440.
An International Preliminary Report on Patentability dated Dec. 10, 2012, which issued during the prosecution of Applicant's PCT/IL2011/000440.
U.S. Appl. No. 60/263,834, filed Jan. 2, 2001.
Sweeney JD et al., "An asymmetric two electrode cuff for generation of unidirectionally propagated action potentials," IEEE Transactions on Biomedical Engineering, vol. BME-33(6) (1986).
An Office Action dated Apr. 9, 2012, which issued during the prosecution of U.S. Appl. No. 12/796,102.
Invitation to pay Additional Fees dated May 10, 2013 which issued during the prosecution of Applicant's PCT/IL2013/005069.
Naples GG et al., "A spiral nerve cuff electrode for peripheral nerve stimulation," by IEEE Transactions on Biomedical Engineering, 35(11) (1988).
Sweeney JD et al., "A nerve cuff technique for selective excitation of peripheral nerve trunk regions," IEEE Transactions on Biomedical Engineering, 37(7) (1990).
Ungar IJ et al., "Generation of unidirectionally propagating action potentials using a monopolar electrode cuff," Annals of Biomedical Engineering, 14:437-450 (1986).

(56) References Cited

OTHER PUBLICATIONS

Fitzpatrick et al., in "A nerve cuff design for the selective activation and blocking of myelinated nerve fibers," Ann. Conf. of the IEEE Eng. in Medicine and Biology Soc, 13(2), 906 (1991).

Rijkhoff NJ et al., "Orderly recruitment of motoneurons in an acute rabbit model," Ann. Conf. of the IEEE Eng., Medicine and Biology Soc., 20(5):2564 (1998).

Van den Honert C et al., "A technique for collision block of peripheral nerve: Frequency dependence," MP-12, IEEE Trans. Biomed. Eng. 28:379-382 (1981).

Baratta R et al., "Orderly stimulation of skeletal muscle motor units with tripolar nerve cuff electrode," IEEE Transactions on Biomedical Engineering, 36(8):836-43 (1989).

Van den Honert C et al., "Generation of unidirectionally propagated action potentials in a peripheral nerve by brief stimuli," Science, 206:1311-1312 (1979).

M. Devor, "Pain Networks", Handbook of Brand Theory and Neural Networks, ED M.A. Arbib MIT Press pp. 696-701, 1998.

Epilepsy center. http://www.bcm.tmc.edu/neural/struct/epilep/epilpsy_vagus.html. May 31, 2011 (2 Versions).

J.F. Cortese, "Vagus Nerve Stimulation for Control of Intractable Epileptic Seizures", May 31, 2001.

An Office Action dated Dec. 5, 2013, which issued during the prosecution of U.S. Appl. No. 13/528,433.

An Office Action dated Sep. 30, 2013, which issued during the prosecution of U.S. Appl. No. 12/796,102.

Chow et al., Evaluation of Cardiovascular Stents as Antennas for Implantable Wireless Applications, IEEE Transactions on Microwave Theory and Techniques, vol. 57, No. 10, Oct. 2009.

Hu et al., Percutaneous Biphasic Electrical Stimulation for Treatment of Obstructive Sleep Apnea Syndrome, IEEE Transactions on Biomedical Engineering, Jan. 2008 vol. 55 Issue:1 p. 181-187—an abstract.

A. Oliven, Electrical stimulation of the genioglossus to improve pharyngeal patency in obstructive sleep apnea: comparison of resultsobtained during sleep and anesthesia, U.S. National Library of Medicine, National Institutes of Health May 2009;148(5):315-9, 350, 349—an abstract.

Mortimer et al., Peripheral Nerve and Muscle Stimulation, Neuroprosthetics Theory and Practice, Chapter 4.2, 2004, p. 632-638.

Zhang, Xu et al. "Mechanism of Nerve Conduction Block Induced by High-Frequency Biphasic Electrical Currents" Biomedical Engineering, IEEE Transactions, 53(12): 2445-2454 (2006).

Zabara J., Inhibition of experimental seizures in canines by repetitive vagal stimulation, Epilepsia. Nov.-Dec. 1992;33 (6):1005-12, http://www.ncbi.nlm.nih.gov/pubmed/1464256—an abstract.

An Office Action dated Jun. 27, 2008, which issued during the prosecution of U.S. Appl. No. 10/205,475.

An Office Action dated Aug. 6, 2009, which issued during the prosecution of U.S. Appl. No. 10/205,475.

An International Search Report and a Written Opinion both dated Jul. 11, 2013, which issued during the prosecution of Applicant's PCT/IL2013/050069.

An International Search Report and a Written Opinion both dated Apr. 29, 2014, which issued during the prosecution of Applicant's PCT/IB2013/060607.

An International Preliminary Report on Patentability dated Jul. 29, 2014, which issued during the prosecution of Applicant's PCT/IL2013/050069.

An International Preliminary Report on Patentability dated Jun. 9, 2015, which issued during the prosecution of Applicant's PCT/IB2013/060607.

A Notice of Allowance dated Apr. 25, 2014, which issued during the prosecution of U.S. Appl. No. 13/528,433.

A Notice of Allowance dated Jun. 9, 2014, which issued during the prosecution of U.S. Appl. No. 12/796,102.

An Office Action dated Sep. 26, 2013, which issued during the prosecution of U.S. Appl. No. 13/528,433.

Takahata, K.; DeHennis, A.; Wise, K.D.; Gianchandani, Y.B., "Stentenna: a micromachined antenna stent for wireless monitoring of implantable microsensors," in Engineering in Medicine and Biology Society, 2003. Proceedings of the 25th Annual International Conference of the IEEE , vol. 4, No., pp. 3360-3363 vol. 4, 17-21.

Spinal Cord Stimulation advanced level (Mayfield clinic)—dated Feb. 2010.

Kaszala, K. and Ellenbogen, K.A., 2010. Device sensing sensors and algorithms for pacemakers and implantable cardioverter defibrillators. Circulation, 122(13), pp. 1328-1340.

Itchkawitz—OC TechInnovation Blog—Electrodes for implantable defibrillator. Printout from http://octechinnovation.com/tag/cameron-health (Downloaded Mar. 2012).

Ebrish, M. et al., Cardiovascular stents as antennas for implantable wireless applications—presentation. BMEN 5151, Apr. 2010.

Abkenari, Lara Dabiri, et al. "Clinical experience with a novel subcutaneous implantable defibrillator system in a single center." Clinical Research in Cardiology 100.9 (2011): 737-744.

Reggiani et al. "Biophysical effects of high frequency electrical field on muscle fibers in culture." (2009) pp. 49-56.

Mushahwar V K et al. "Muscle recruitment through electrical stimulation of the lumbo-sacral spinal cord," IEEE Trans Rehabil Eng, 8(1):22-9 (2000).

An Office Action dated Jan. 5, 2007, which issued during the prosecution of U.S. Appl. No. 10/722,589.

An Office Action dated May 14, 2008, which issued during the prosecution of U.S. Appl. No. 10/722,589.

An Office Action dated Mar. 17, 2010, which issued during the prosecution of U.S. Appl. No. 10/722,589.

Deurloo K E et al., "Transverse tripolar stimulation of peripheral nerve: a modelling study of spatial selectivity," Med Biol Eng Comput, 36(1):66-74 (1998).

Tarver W B et al. "Clinical experience with a helical bipolar stimulating lead," Pace, vol. 15, October, Part II (1992).

Agnew W F et al. "Microstimulation of the lumbosacral spinal cord," Huntington Medical Research Institutes Neurological Research Laboratory, Sep. 30, 1995-Sep. 29, 1998.

Grill W M et al. "Inversion of the current-distance relationship by transient depolarization," IEEE Trans Biomed Eng, 44 (1):1-9 (1997).

Goodall E V et al., "Position-selective activation of peripheral nerve fibers with a cuff electrode," IEEE Trans Biomed Eng, 43(8):851-6 (1996).

Veraart C et al., "Selective control of muscle activation with a multipolar nerve cuff electrode," IEEE Trans Biomed Eng, 40(7):640-53 (1993).

Rattay, F., (1989) "Analysis of models for extracellular fiber stimulation," IEEE Transactions on Biomedical Engineering, 36(2): 676-682.

Jones, J.F.X. et al., (1998) "Activity of C Fibre Cardiac Vagal Efferents in Anaesthetized Cats and Rats," Journal of Physiology, 507(3) 869-880.

Shealy (1967) Electrical inhibition of pain by stimulation of the dorsal columns.

Nov. 30, 2015 massdevice.com—St. Jude Medical's Proclaim Elite debuts in Europe.

Kaplan et al. (2009) Design and fabrication of an injection tool for neuromuscular microstimulators.

Supplementary European Search Report dated Dec. 22, 2014, which issued during the prosecution of Applicant's European App No. 11792044.7.

An Office Action dated Oct. 30, 2015, which issued during the prosecution of U.S. Appl. No. 14/226,723.

Lind (2012) Advances in spinal cord stimulation.

U.S. Appl. No. 60/985,353, filed Nov. 5, 2007.

Brindley (1983) A technique for anodally blocking large nerve fibers.

Robert Szmurlo, Jacek Starzynski, Stanislaw Wincenciak, Andrzej Rysz, (2009) "Numerical model of vagus nerve electrical stimulation", COMPEL—The international journal for computation and mathematics in electrical and electronic engineering, vol. 28 Iss: 1, pp. 211-220.

(56) References Cited

OTHER PUBLICATIONS

Filiz, Sinan, et al. "Micromilling of microbarbs for medical implants." International Journal of Machine Tools and Manufacture 48.3 (2008): 459-472.
Mitchum, A Shocking Improvement in Cardiology Science Life Blog, University of Chicago, http://sciencelife.uchospitals.edu/2010/04/13/a-shocking-improvement-in-cardiology/ (Downloaded Nov. 3, 2012).
Bluemel, K.M, "Parasympathetic postganglionic pathways to the sinoatrial node," J Physiol. 259 (5 Pt 2): H1504-10 (1990).
Bibevski, S. etal. "Ganglionic Mechanisms Contribute to Diminished Vagal Control in Heart Failure," Circulation 99:2958-2963(1999).
Chen, S.A. et al., "Intracardiac stimulation of human parasympathetic nerve fibers induces negative dromotropic effects: implication with the lesions of radiofrequency catheter ablation," J Cardiovasc Electrophysiol. 9(3):245-52 (1998).
Cooper et al., "Neural effects on sinus rate and atrial ventricular conduction produced by electrical stimulation from a transvenous electrode catheter in the canine right pulmonary artery" Circ Res vol. 46(1):48-57 (1980).
Waninger, M.S. etal., "Electrophysiological control of ventricular rate during atrial fibrillation," Pace 23:1239-1244 (2000).
Goldberger, J.J. et al., "New technique for vagal nerve stimulation," J Neurosci Methods. 91(1-2):1089-14 (1999).
Carlson, M.D. et al., "Selective stimulation of parasympathetic nerve fibers to the human sinoatrial node," Circulation 85:1311-1317 (1992).
Page, P.L. et al., "Regional distribution of atrial electrical changes induced by stimulation of extracardiac and intracardia neural elements," J. Thorac Cardiovasc Surg. 109{2}:377-388 (1995).
Zi-Ping, Fang, et al., (1991) "Selective Activation of Small Motor Axons by Quasitrapezodial Current Pulses", IEEE Transactions on Biomedical Engineering 38(2): 168-171.
An Office Action dated Nov. 1, 2007, which issued during the prosecution of U.S. Appl. No. 10/205,475.
An Office Action dated Apr. 5, 2007, which issued during the prosecution of U.S. Appl. No. 10/488,334.
An Office Action dated Apr. 25, 2008, which issued during the prosecution of U.S. Appl. No. 10/488,334.
An Office Action dated Dec. 26, 2008, which issued during the prosecution of U.S. Appl. No. 10/488,334.
Rijkhof, N. J. M. et al. "Acute Animal Studies on the Use of Anodal Block to Reduce Urethral Resistance in Sacral Root Stimulation,", IEEE Transactions on Rehabilitation Engineering, vol. 2, No. 2, pp. 92, 1994.
An Office Action dated Apr. 7, 2006, which issued during the prosecution of U.S. Appl. No. 10/722,589.
https://www.uroplasty.com/files/pdf/20158.pdf Brochure (Downloaded Oct. 16, 2014).
An Office Action dated Jan. 23, 2003, which issued during the prosecution of U.S. Appl. No. 09/824,682.
Jones et al. "Heart rate responses to selective stimulationof cardiac vagal fibres in anaesthetized cats, rats and rabbits" Journal of Physiology 1995;489; 203-214.
Wallick, Don W. et al "Selective AV nodal vagal stimulation improves hemodynamics during acute atrial fibrillation in dogs", Am J. Physiol Heart Circ Physiol, 281: H1490-H1497, 2001.
Tsuboi, Masato et al., "Inotropic, chronotropic and dromotropic effects mediated via parasympathetic ganglia in the dog heart", Am J. Physiol Heart Circ Physiol, 279: H1201-H1207, 2000.
Chiou, C.W. et al., "Efferent vagal innervation of the canine atria and sinus and atrioventricular nodes", Circulation, 1997; 95:2573.
Schauerte, P. et al, "Catheter stimulation of cariac parasympathetic nerves in humans", available at http://www.circulationaha.org, pp. 2430-2435, 2001.
Hirose, M. "Pituitary adenylate cyclase-activating polypeptide-27 causes a biphasic chronotropic effect and atrial fibrillation in autonomically decentralized, anesthetized dogs", The Journal of Pharmacology and Experimental Therapeutics, vol. 283, No. 2, pp. 478-487, 1997.
An Office Action dated Jul. 17, 2002, which issued during the prosecution of U.S. Appl. No. 09/824,682.
An Advisory Action dated Mar. 4, 2003, which issued during the prosecution of U.S. Appl. No. 09/824,682.
Garrigue, S. et al., "Post-ganglionic vagal stimulation of the atrioventricular node reduces ventricular rate during atrial fibrillation," Pace 21(4), Part II, 878 (1998).
Furukawa, Y. et al., "Differential blocking effects of atropine and gallamine on negative chrontropic and dromotropic responses to vagus stimulation in anesthetized dogs," J Pharmacol Exp. Ther. 251(3):797-802 (1989).
European Office Action, dated Apr. 3, 2009, in connection with European Patent Application No. 02716294.0.
Tuday, Eric C. et al. "Differential activation of nerve fibers with magnetic stimulation in humans" BMC Neuroscience, 7: 58. Published online Jul. 24, 2006. doi: 10.1186/1471-2202-7-58.
Stampfli, Robert, 1954. Saltatory conduction in nerve 1. Physiol. Rev. 34: 101-112.
Schaldach, M, "New concepts in electrotherapy of the heart", Electrotherapy of the Heart, Springer Verlag Heidelberg, pp. 210-214 (1992).
An Office Action dated Apr. 4, 2017, which issued during the prosecution of U.S. Appl. No. 14/601,604.
An Office Action dated Apr. 5, 2017, which issued during the prosecution of U.S. Appl. No. 14/374,375.
Notice of Allowance dated Sep. 1, 2017, which issued during the prosecution of U.S. Appl. No. 14/649,873.

* cited by examiner

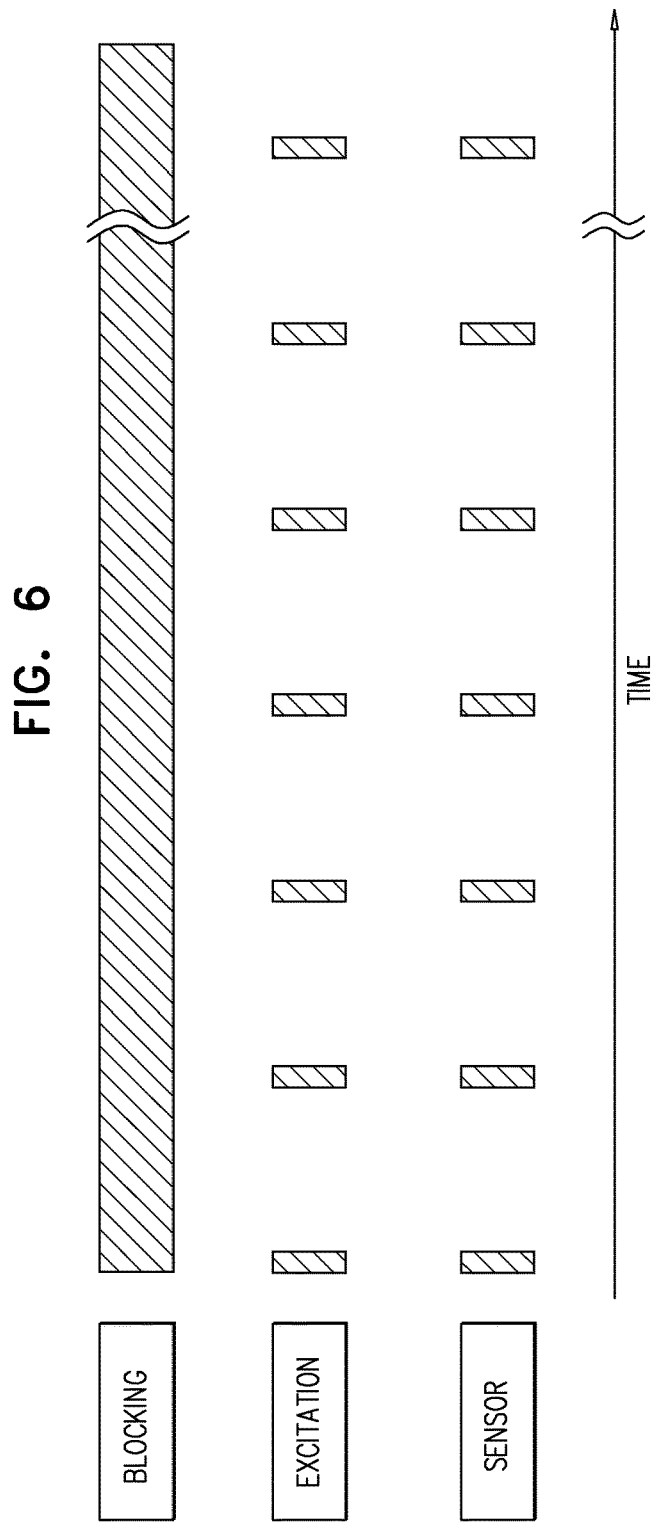

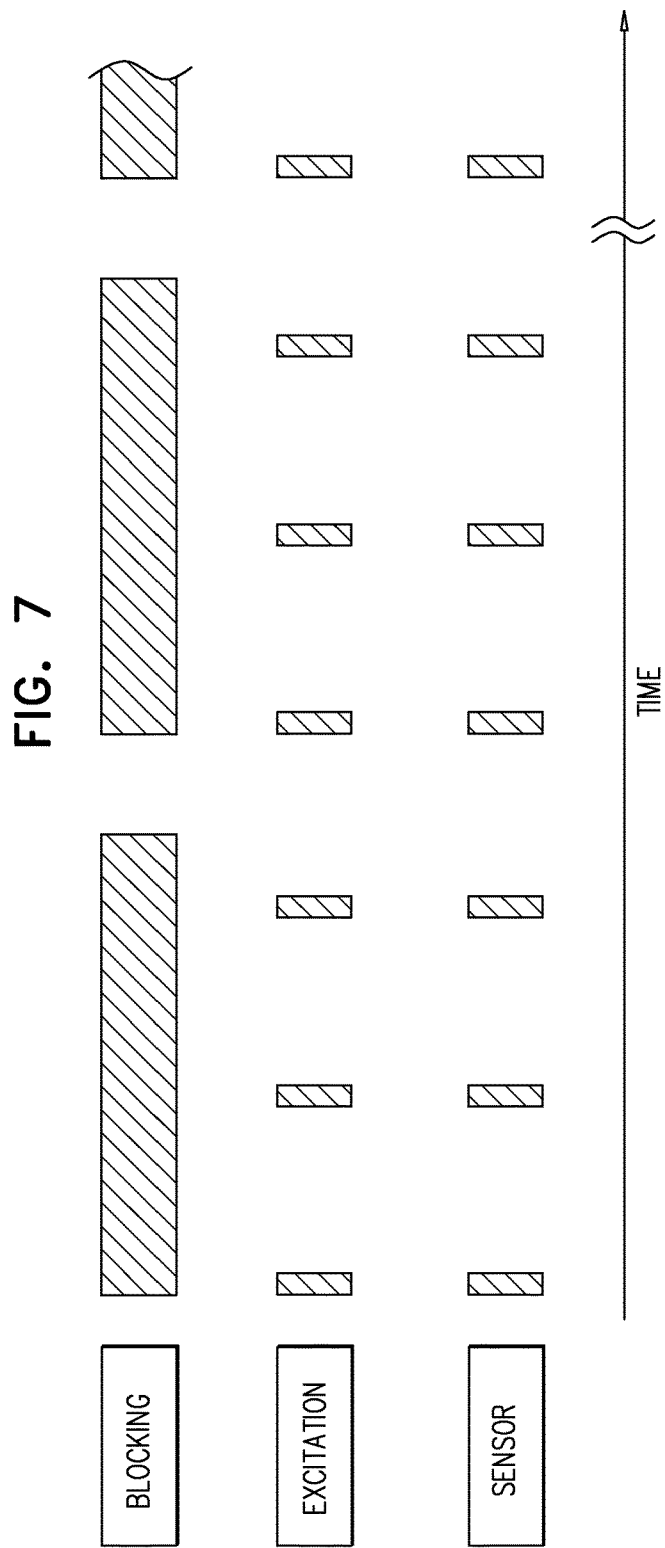

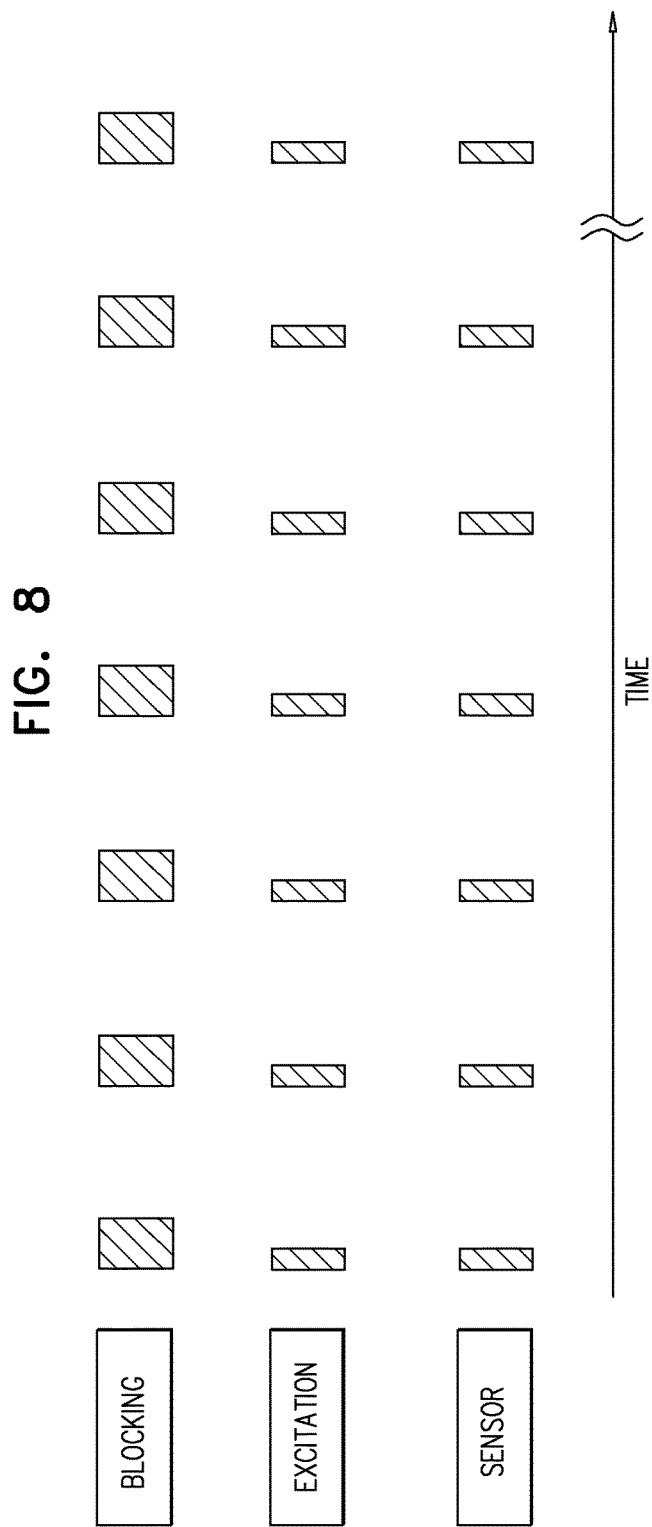

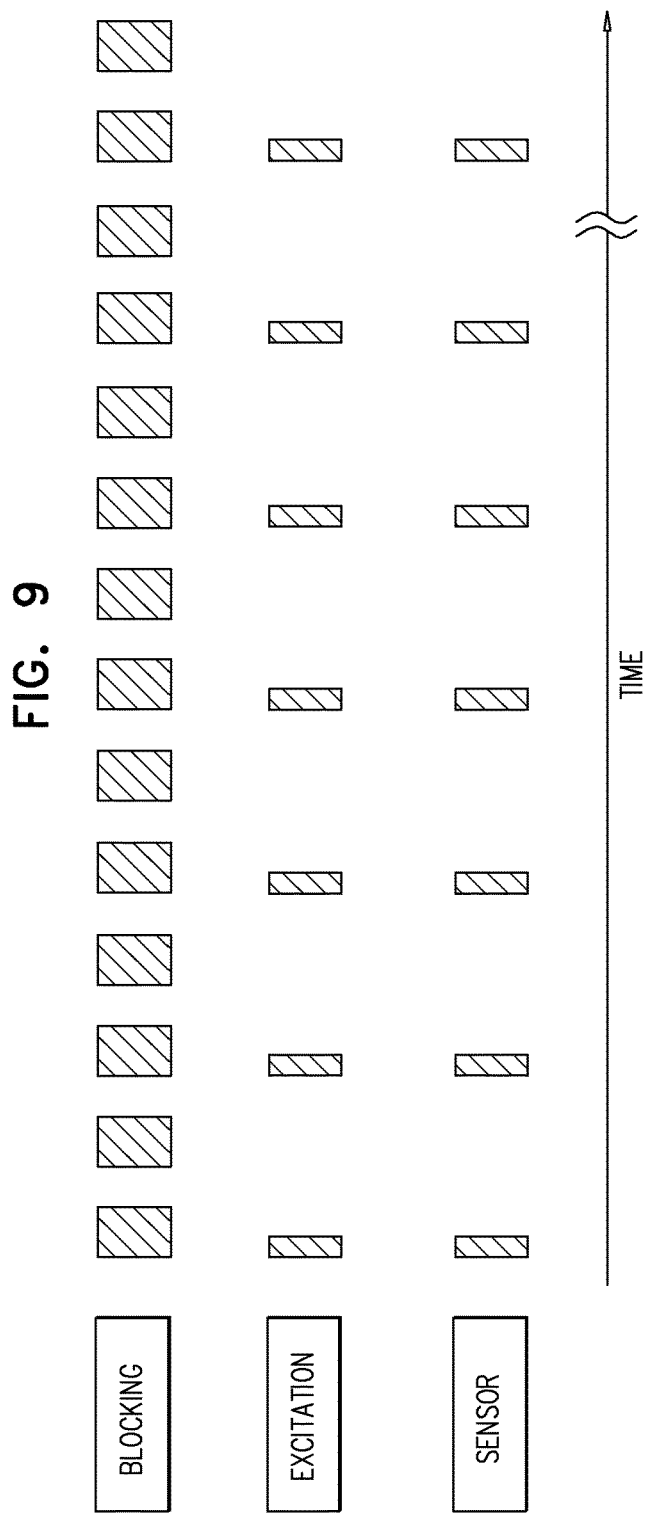

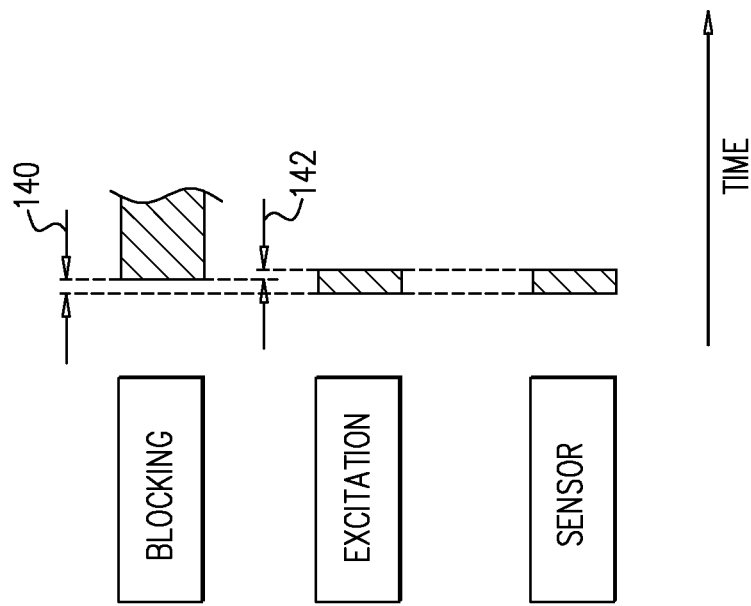

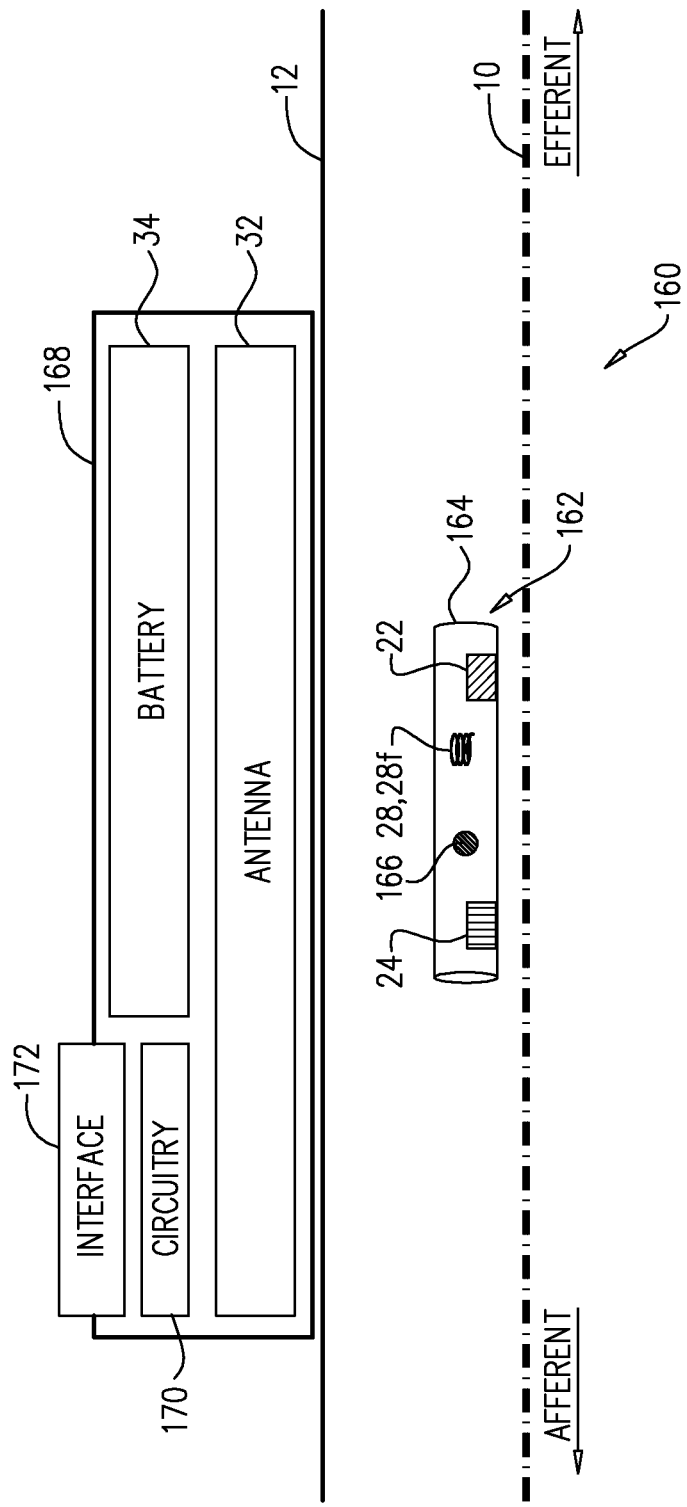

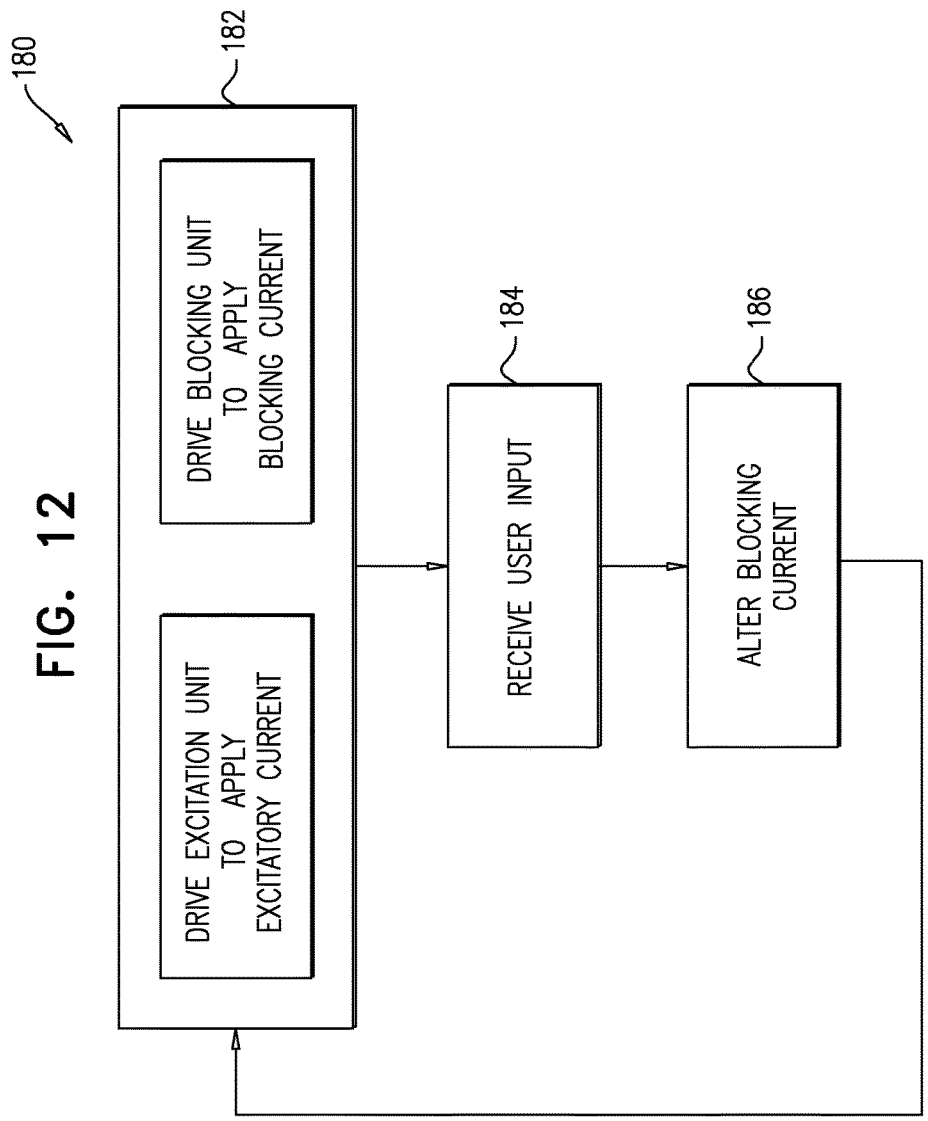

OPTIMIZATION OF APPLICATION OF CURRENT

CROSS-REFERENCES TO RELATED APPLICATIONS

The present application is related to the following applications, all of which are assigned to the assignee of the present application, and all of which are incorporated herein by reference:

U.S. patent application Ser. No. 14/374,375 to Gross et al., entitled "Wireless neurostimulators," which published as US 2015/0018728;

U.S. patent application Ser. No. 14/601,626 to Oron et al., filed Jan. 21, 2015, and entitled "Extracorporeal implant controllers", which published as US 2016/0206890; and U.S. patent application Ser. No. 14/601,568 to Plotkin et al., filed Jan. 21, 2015, and entitled "Transmitting coils for neurostimulation", which published as US 2016/0206889 (now U.S. Pat. No. 9,597,521).

FIELD OF THE INVENTION

Some applications of the present invention relate in general to medical devices. More specifically, some applications of the present invention relate to percutaneous neurostimulator implants.

BACKGROUND

Neurostimulation is a clinical tool used to treat various neurological disorders. This technique involves modulation of the nervous system by electrically activating fibers in the body. Percutaneous implants exist for providing neurostimulation. Powering such implants is a technical challenge.

SUMMARY OF THE INVENTION

Systems described herein comprise a blocking unit that is configured to block undesired endogenous action potentials, typically afferent action potentials that cause an unpleasant or painful sensation, e.g., due to neuropathy.

Calibration of nerve-blocking devices is useful because the parameters of the blocking current required for effective blocking of action potentials may differ between individual subjects themselves, and/or due to differences in the position and orientation of the device, e.g., with respect to the target nerve. Furthermore, for devices that comprise an implant, movement of the implant (e.g., long-term migration, or short-term movement due to movement of the subject) may also affect the optimal parameters of the blocking current.

Several of the techniques described herein involve calibrating the nerve-blocking device, facilitated by artificially-induced action potentials, thereby overcoming the problem described above. For some of these techniques, the artificially-induced action potentials are detected by a sensor unit, and calibration is automated. For some techniques, the calibration is manual. For some applications of the invention, calibration is performed only before treatment (e.g., by a physician). For some applications of the invention, calibration is performed regularly (e.g., several times per week, day or hour).

There is therefore provided, in accordance with an application of the present invention, apparatus, for use with a nerve of a subject, the apparatus including:

an implantable excitation unit, configured to induce action potentials in the nerve by applying an excitatory current to the nerve;

an implantable blocking unit, configured to block the induced action potentials from propagating along the nerve by applying a blocking current to the nerve; and an extracorporeal controller, including (i) at least one antenna, and (ii) circuitry configured:

to wirelessly drive the excitation unit to apply the excitatory current, in a first mode of the extracorporeal controller, to wirelessly drive the blocking unit to apply the blocking current while not driving the excitation unit to apply the excitatory current, in a second mode of the extracorporeal controller, to wirelessly drive the blocking unit to apply the blocking current while driving the excitation unit to apply the excitatory current, and to wirelessly alter a parameter of the blocking current, based on sensing performed while the extracorporeal controller is in the second mode.

In an application, the circuitry is configured to automatically periodically switch the extracorporeal controller between the first and second modes.

In an application, the apparatus further includes an implant that includes a housing that houses the excitation unit and the blocking unit.

In an application, the circuitry is configured, in a third mode of the extracorporeal controller, to wirelessly drive the excitation unit to apply the excitatory current while not driving the blocking unit to apply the blocking current.

In an application, the excitatory current has a frequency of 2-400 Hz, and the circuitry is configured to wirelessly drive the excitation unit to apply the excitatory current having the frequency of 2-400 Hz.

In an application, the excitatory current has a frequency of 5-100 Hz, and the circuitry is configured to wirelessly drive the excitation unit to apply the excitatory current having the frequency of 5-100 Hz.

In an application, the blocking current has a frequency of 1-20 kHz, and the circuitry is configured to wirelessly drive the blocking unit to apply the blocking current having the frequency of 1-20 kHz.

In an application, the blocking current has a frequency of 3-10 kHz, and the circuitry is configured to wirelessly drive the blocking unit to apply the blocking current having the frequency of 3-10 kHz.

In an application, the apparatus further includes an implantable sensor unit, configured to detect the induced action potentials in the nerve, and to responsively provide a sensor signal that conveys information about the detected induced action potentials, and the circuitry of the extracorporeal controller is configured to wirelessly receive the sensor signal, and to alter the parameter of the blocking current in response to the received sensor signal.

In an application, the apparatus further includes an implant that includes a housing that houses the excitation unit, the blocking unit, and the sensor unit.

In an application, the circuitry is configured to automatically periodically run a calibration routine including:

(a) switching the extracorporeal controller into the second mode, (b) receiving the sensor signal, the sensor signal conveying information about induced action potentials detected while the extracorporeal controller is in the second mode, (c) in response to the sensor signal received in step (b) of the calibration routine, altering the parameter of the blocking current, and (d) switching the extracorporeal controller into the first mode.

In an application, the circuitry is configured, in a third mode of the extracorporeal controller, to wirelessly drive the excitation unit to apply the excitatory current while not driving the excitation unit to apply the blocking current, and the calibration routine further includes, prior to step (a):

(i) switching the extracorporeal controller into the third mode, and (ii) receiving the sensor signal, the sensor signal conveying information about induced action potentials detected while the extracorporeal controller is in the third mode.

In an application, step (c) of the calibration routine includes altering the parameter of the blocking current in response to the sensor signal received in step (b) of the calibration routine, and in response to the sensor signal received in step (ii) of the calibration routine.

In an application, the extracorporeal controller further includes a user interface, and the circuitry is configured to wirelessly alter the parameter of the blocking current in response to user operation of the user interface.

In an application, the circuitry is configured to switch the extracorporeal controller between the first and second modes in response to user operation of the user interface.

There is further provided, in accordance with an application of the present invention, apparatus for use with a nerve of a subject, the apparatus including:

an excitation unit, configured to induce action potentials in the nerve by applying an excitatory current to the nerve;

an implantable blocking unit, configured to block the induced action potentials from propagating along the nerve by applying a blocking current to the nerve;

an implantable sensor unit, configured to detect the induced action potentials in the nerve, and to responsively provide a sensor signal that conveys information about the detected induced action potentials; and circuitry configured:
to drive the excitation unit to apply the excitatory current,
to drive the blocking unit to apply the blocking current,
while driving the blocking unit to apply the blocking current, to drive the sensor unit to detect the induced action potentials and provide the sensor signal,
to receive the sensor signal, and
in response to the sensor signal, to alter a parameter of the blocking current.

In an application, the apparatus further includes an extracorporeal controller that includes the circuitry, and is configured to wirelessly drive the excitation unit, the blocking unit, and the sensor unit, and to wirelessly receive the sensor signal.

In an application, the sensor signal is a wireless sensor signal, and the circuitry is configured to wirelessly receive the sensor signal.

In an application, the circuitry is configured to drive the excitation unit wirelessly, and to drive the blocking unit wirelessly.

In an application, the excitation unit is configured to elicit paresthesia by applying the excitatory current.

In an application, the excitation unit is configured to elicit pain by applying the excitatory current.

In an application, the circuitry is configured to automatically periodically run a calibration routine including:

(a) switching from (i) a first mode in which the circuitry drives the blocking unit to apply the blocking current while not driving the excitation unit to apply the excitatory current, into (ii) a second mode in which the circuitry drives the blocking unit to apply the blocking current while driving the excitation unit to apply the blocking current, (b) while in the second mode, driving the sensor unit to detect the induced action potentials and provide the sensor signal, (c) in response to the sensor signal received in (b), altering the parameter of the blocking current, and (d) switching back into the first mode.

In an application, the circuitry is configured:

to drive the blocking unit by providing a blocking-command signal having an energy consumption; and in response to the sensor signal conveying information indicative of a reduction of detected induced action potentials, to reduce the energy consumption of the blocking-command signal.

In an application, the blocking unit is disposed between the excitation unit and the sensor unit.

In an application, the excitation unit is an implantable excitation unit.

In an application, the excitatory current has a lower frequency than that of the blocking current, and the circuitry is configured to drive the excitation unit to apply the excitatory current having the lower frequency.

In an application, the excitatory current has a frequency of 2-400 Hz, and the circuitry is configured to drive the excitation unit to apply the excitatory current having the frequency of 2-400 Hz.

In an application, the excitatory current has a frequency of 5-100 Hz, and the circuitry is configured to drive the excitation unit to apply the excitatory current having the frequency of 5-100 Hz.

In an application, the blocking current has a frequency of 1-20 kHz, and the circuitry is configured to drive the blocking unit to apply the blocking current having the frequency of 1-20 kHz.

In an application, the blocking current has a frequency of 3-10 kHz, and the circuitry is configured to drive the blocking unit to apply the blocking current having the frequency of 3-10 kHz.

In an application, the apparatus further includes an implant that includes the excitation unit, the blocking unit, and the sensor unit.

In an application, the apparatus further includes an extracorporeal controller that includes the circuitry, and is configured to wirelessly drive the excitation unit, the blocking unit, and the sensor unit, and to wirelessly receive the sensor signal.

In an application, the implant further includes the circuitry.

In an application, the implant is injectable.

In an application, the implant is dimensioned to be injectable into an epidural space of a subject.

In an application, the implant is configured to be implanted at the nerve such that the sensor unit is disposed at a first nerve site, and the blocking unit is disposed at a second nerve site that is efferent to the first nerve site.

In an application:

the implant has a longitudinal axis, the blocking unit is 0.5-5 cm along the longitudinal axis from the excitation unit, and the sensor unit is 0.5-5 cm along the longitudinal axis from the blocking unit.

There is further provided, in accordance with an application of the present invention, apparatus, for use with a nerve of a subject, the apparatus including:

an implant, having a longitudinal axis, injectable into the subject along the longitudinal axis, and including:
an elongate housing having a first half including a first end, and a second half including a second end;
at least one paresthesia-inducing electrode disposed on a first site of the housing within the first half;
at least one blocking electrode disposed on a second site of the housing within the second half; and
circuitry, having:
a first mode in which the circuitry simultaneously drives (i) the at least one paresthesia-inducing electrode to apply a paresthesia-inducing current having a frequency of 2-400 Hz, and (ii) the at least one blocking electrode to apply a blocking current having a frequency of 1-20 kHz, and
a second mode in which the circuitry (i) drives the at least one blocking electrode to apply the blocking current, but (ii) does not drive the at least one paresthesia-inducing electrode to apply the paresthesia-inducing current.

The present invention will be more fully understood from the following detailed description of applications thereof, taken together with the drawings, in which:

BRIEF DESCRIPTION OF THE DRAWINGS

FIGS. 5-10 are schematic illustrations illustrating the operation of the systems, in accordance with some applications of the invention; and FIGS. 11-12 are schematic illustrations of a system for use with a nerve of a subject, and operation of the system, in accordance with some applications of the invention.

DETAILED DESCRIPTION OF EMBODIMENTS

Figure 1:
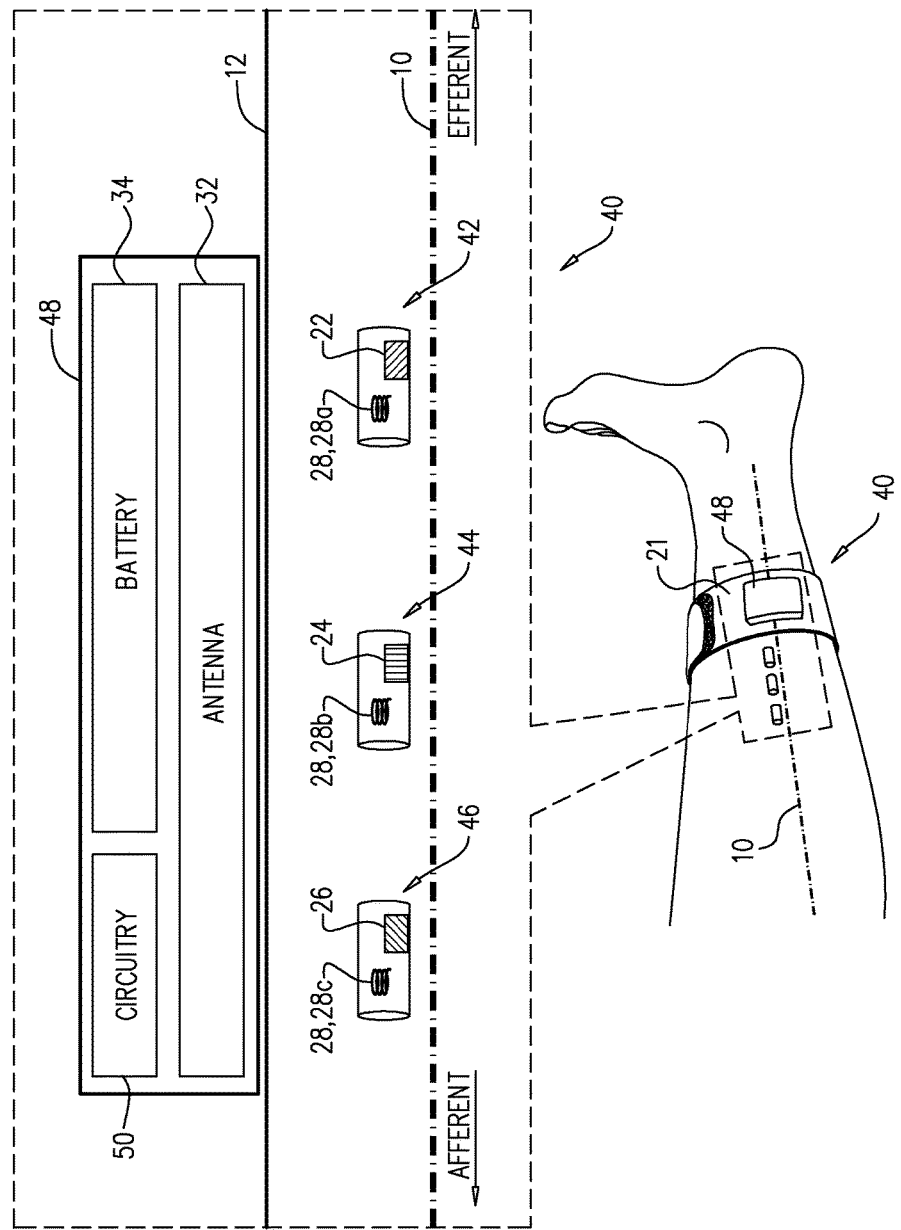
FIGS. 1-4 are schematic illustrations of systems for use with a nerve of a subject, in accordance with some applications of the invention.

Systems described herein, comprise a blocking unit that is configured to block undesired endogenous action potentials, typically afferent action potentials that cause an unpleasant or painful sensation, e.g., due to neuropathy. For some applications, this is the primary function of the system.

Calibration of nerve-blocking devices is useful because the parameters of the blocking current required for effective blocking of action potentials may differ between individual subjects themselves, and/or due to differences in the position and orientation of the device, e.g., with respect to the target nerve. Furthermore, for devices that comprise an implant, movement of the implant (e.g., long-term migration, or short-term movement due to movement of the subject) may also affect the optimal parameters of the blocking current.

Typically, calibration of a nerve-blocking device is performed based on feedback from the subject regarding whether a reduction in the unpleasant/painful sensation has been achieved. Often, the sensation being treated is not continuous or constant, and may fluctuate based on time of day, position and/or activity of the subject, and/or other factors. This can make such calibration difficult. Several of the techniques described herein involve calibrating the nerve-blocking device, facilitated by artificially induced action potentials, thereby overcoming the problem described above.

Reference is made to FIGS. 1-4, which are schematic illustrations of systems 40, 60, 80 and 100 for use with a nerve of a subject, in accordance with some applications of the invention. Each of systems 40, 60, 80 and 100 comprises (i) an implantable excitation unit, configured to induce action potentials in the nerve by applying an excitatory current to the nerve, (ii) an implantable blocking unit, configured to block the induced action potentials from propagating along the nerve by applying a blocking current to the nerve, (iii) an implantable sensor unit, configured to detect the induced action potentials, and (iv) circuitry configured, inter alia, to drive the excitation unit, the blocking unit, and the sensor unit. Each of systems 40, 60 and 80 further comprises an extracorporeal controller that wirelessly powers the excitation unit, the blocking unit, and the sensor unit. The extracorporeal controller of systems 40 and 60 further comprise the circuitry that is configured to drive the excitation unit, the blocking unit, and the sensor unit, whereas in system 80 that circuitry is implantable, and the extracorporeal controller wirelessly provides only power. In system 100, power is provided by an implanted battery, and there is no extracorporeal controller.

The excitation unit, the blocking unit, and the sensor unit each comprise one or more electrodes, and each is therefore configured to interface electrically with the subject. The excitation unit applies the excitatory current via its one or more electrodes, the blocking unit applies the blocking current via its one or more electrodes, and the sensor unit detects the induced action potentials via its one or more electrodes.

Typically, the blocking current has a frequency of greater than 1 kHz, and/or less than 20 kHz (e.g., 1-20 kHz, e.g., 1-10 kHz, such as 3-10 kHz).

Typically, the excitatory current has a frequency of greater than 2 Hz and/or less than 400 Hz (e.g., 2-400 Hz, e.g., 2-300 Hz, e.g., 2-200 Hz, e.g., 2-100 Hz, e.g., 5-100 Hz, e.g., 5-40 Hz). For some applications, the excitatory current includes bursts of higher-frequency such as up to 1200 Hz. Typically, the excitatory current has a frequency that is lower than that of the blocking current. Typically, the excitatory current is configured to induce action potentials that, at least in the absence of the blocking current, are experienced by the subject, e.g., as a sensation such as paresthesia or pain. For some applications, the excitatory current is configured to induce action potentials that are not experienced by the subject (e.g., as a sensation).

The excitation unit of each system is configured to induce afferent action potentials, which are detected by the sensor unit. The sensor unit provides (wirelessly or wiredly) a sensor signal that conveys information about the detected action potentials (e.g., their magnitude and/or frequency). The circuitry of the system is configured to receive the sensor signal, and to responsively alter a parameter of the blocking current, such as amplitude, frequency or duty cycle. Thereby, the circuitry establishes the effectiveness of the blocking unit and/or blocking current at blocking the induced action potentials, and calibrates the blocking current to an effective but not excessive level, thereby optimizing power consumption, as well as the amount of current received by the subject.

FIGS. 1-4 show the respective system with respect to a nerve 10 and skin 12 of a subject. The labels "AFFERENT" and "EFFERENT" indicate the orientation of the neural anatomy. Nerve 10 is typically a peripheral nerve. For some applications nerve 10 is a spinal nerve. For some applications nerve 10 is nervous tissue of the spinal cord, and the implant(s) are implanted in (e.g., injected into) the epidural space.

FIG. 1 shows system 40, which comprises (i) an implantable excitation unit 22, configured to induce action potentials in the nerve by applying an excitatory current to the nerve, (ii) an implantable blocking unit 24, configured to block the induced action potentials from propagating along the nerve by applying a blocking current to the nerve, (iii) an implantable sensor unit 26, configured to detect the induced action potentials, and (iv) circuitry 50 configured, inter alia, to drive the excitation unit, the blocking unit, and the sensor unit.

System 40 comprises (i) an excitation implant 42 that comprises excitation unit 22, as well as an intracorporeal antenna 28 (labeled 28*a*), (ii) a blocking implant 44 that comprises blocking unit 24, as well as an intracorporeal antenna 28 (labeled 28*b*), and (iii) a sensor implant 46 that comprises sensor unit 26, as well as an intracorporeal antenna 28 (labeled 28*c*). Typically, each of the implants comprises a housing that houses the respective unit. The implants are typically implanted in the vicinity (e.g., within 10 mm, such as within 7 mm) of nerve 10. The implants are implanted such that, as shown, implant 46 is afferent to implant 44, and implant 44 is afferent to implant 42 (and therefore unit 26 is afferent to unit 24, and unit 24 is afferent to unit 22). Typically, implants 42, 44 and 46 are implanted by injection, and may be implanted independently or using a single injection device.

For some applications, implant 46 is implanted 1-10 cm (e.g., 2-5 cm) away from implant 44, and implant 44 is implanted 1-10 cm (e.g., 2-5 cm) away from implant 42.

System 40 further comprises an extracorporeal controller 48 that comprises circuitry 50, as well as an extracorporeal antenna 32 and a battery 34 that powers the circuitry. (It is to be understood that antenna 32 may comprise one or more antennas.) Circuitry 50 is configured to wirelessly drive (e.g., to wirelessly power and operate) excitation unit 22, blocking unit 24, and sensor unit 26, via antenna 32 and antennas 28. Units 22, 24 and 26 (e.g., implants 42, 44 and 46) are independently addressable by extracorporeal controller 48 (e.g., by circuitry 50 thereof). For example, a wireless power signal having a particular characteristic (e.g., frequency) may be used when a particular unit is to be driven, and only that unit is powered by that power signal (e.g., only the antenna of the implant of that unit is configured to receive that power signal). Similarly, a code may be modulated onto the power signal.

The operation of system 40 (as well as that of systems 60, 80 and 100) will be described hereinbelow (e.g., with reference to FIGS. 5-10).

Figure 2:
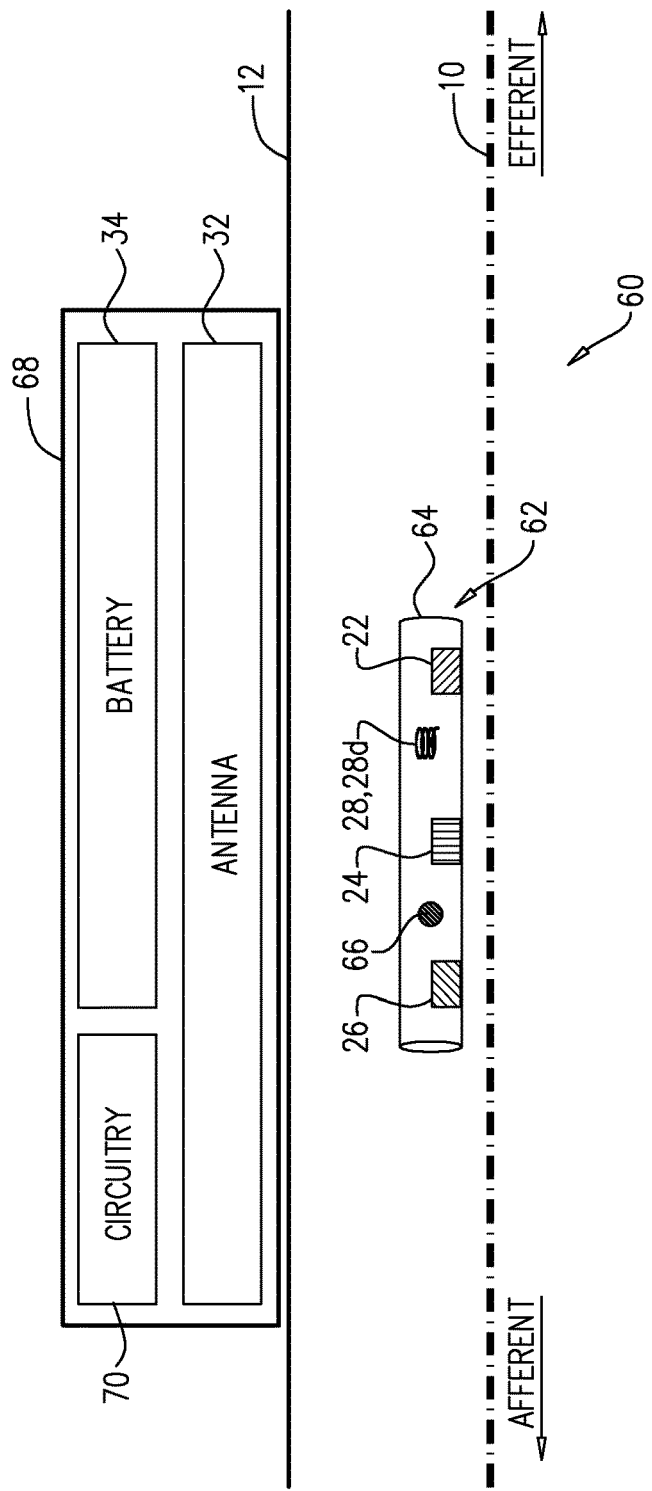

FIG. 2 shows system 60, which comprises excitation unit 22, blocking unit 24, sensor unit 26, and circuitry 70 configured, inter alia, to drive the excitation unit, the blocking unit, and the sensor unit.

System 60 comprises an implant 62 that comprises excitation unit 22, blocking unit 24, and sensor unit 26, as well as an intracorporeal antenna 28 (labeled 28*d*). Typically, implant 62 comprises a housing 64 that houses units 22, 24 and 26, and antenna 28*d*. Housing 64 is typically elongate. Typically, implant 62 is implanted in the vicinity (e.g., within 10 mm, such as within 7 mm) of nerve 10, e.g., such that a longitudinal axis of the implant is aligned with the nerve. Implant 62 is implanted such that unit 26 is afferent to unit 24, and unit 24 is afferent to unit 22. Typically, implant 62 is implanted by injection.

For some applications, implant 62 is dimensioned such that unit 26 (e.g., the electrode(s) thereof) is 0.5-5 cm (e.g., 1-2 cm) away from unit 24 (e.g., the electrode(s) thereof). For some applications, implant 62 is dimensioned such that unit 24 (e.g., the electrode(s) thereof) is 0.5-5 cm (e.g., 1-2 cm) away from unit 22 (e.g., the electrode(s) thereof).

System 60 further comprises an extracorporeal controller 68 that comprises circuitry 70, as well as extracorporeal antenna 32 and battery 34 that powers the circuitry. Circuitry 70 is configured to wirelessly drive (e.g., to wirelessly power and operate) excitation unit 22, blocking unit 24, and sensor unit 26, via antenna 32 and antenna 28*d*. Units 22, 24 and 26 are independently addressable by extracorporeal controller 68 (e.g., by circuitry 70 thereof). For example, a code may be modulated onto the wireless power signal, and implant 62 may comprise implant circuitry 66 (e.g., comprising a switch), which directs the received power to the appropriate unit in response to the code. Alternatively, implant 62 may comprise a separate antenna for each of units 22, 24 and 26 (e.g., as shown for system 20, mutatis mutandis), and the wireless power signal is configured to have a particular characteristic (e.g., frequency) that only a particular antenna is configured to receive.

Therefore, for some applications of the invention, system 60 is similar to system 20, except that units 22, 24 and 26 are housed within a single implant, rather than within separate implants.

The operation of system 60 (as well as that of systems 40, 80 and 100) will be described hereinbelow (e.g., with reference to FIGS. 5-10).

Figure 3:
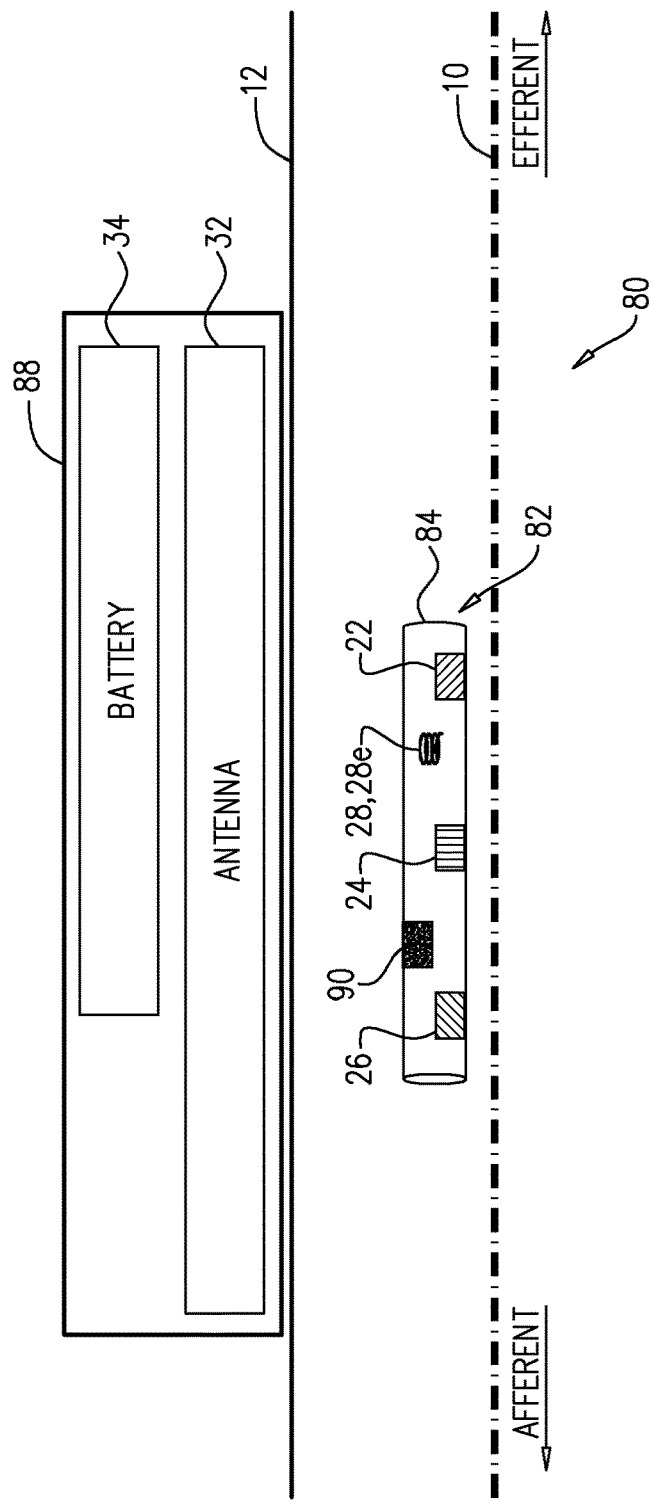

FIG. 3 shows system 80, which comprises excitation unit 22, blocking unit 24, sensor unit 26, and circuitry 90 configured, inter alia, to drive the excitation unit, the blocking unit, and the sensor unit.

System 80 comprises an implant 82 that comprises excitation unit 22, blocking unit 24, and sensor unit 26, as well as an intracorporeal antenna 28 (labeled 28*e*). In this regard, system 80 is identical to system 60. However, whereas in system 60 (and system 40) the circuitry that drives units 24, 26 and 28 is within an extracorporeal controller, in system 80 implant 82 comprises circuitry 90. That is, circuitry 90 is implant circuitry. Typically, implant 82 comprises a housing 84 that houses units 22, 24 and 26, antenna 28*e*, and circuitry 90. Housing 84 is typically elongate. Typically, implant 82 is implanted in the vicinity (e.g., within 10 mm, such as within 7 mm) of nerve 10, e.g., such that a longitudinal axis of the implant is aligned with the nerve. Implant 82 is implanted such that unit 26 is afferent to unit 24, and unit 24 is afferent to unit 22. Typically, implant 82 is implanted by injection.

System 80 further comprises an extracorporeal controller 88 that comprises extracorporeal antenna 32 and battery 34. Whereas in systems 40 and 60, the extracorporeal controller (e.g., circuitry thereof) drives units 22, 24 and 26, in system 80 controller 88 merely provides wireless power to implant 82 via antennas 32 and 28*e*. That is, controller 88 wirelessly powers circuitry 90, which drives (e.g., operates, typically wiredly) units 22, 24 and 26. Units 22, 24 and 26 are independently addressable by circuitry 90.

Therefore, for some applications of the invention, system 80 is similar to system 60, except that the circuitry that drives units 24, 26 and 28 is within the implant, rather than within the extracorporeal controller.

The operation of system 80 (as well as that of systems 40, 60 and 100) will be described hereinbelow (e.g., with reference to FIGS. 5-10).

Figure 4:
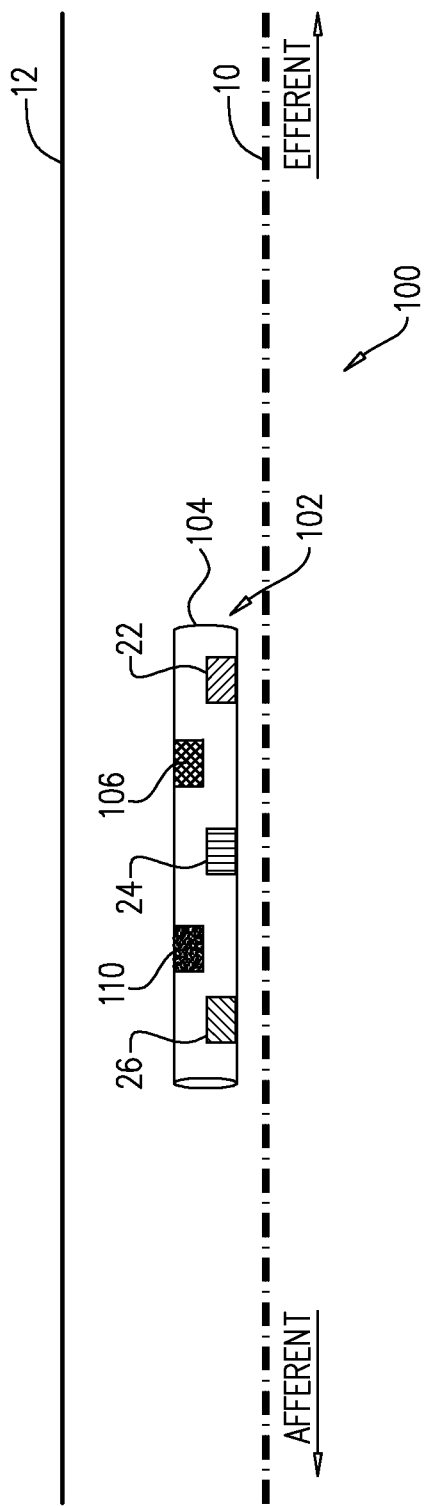

FIG. 4 shows system 100, which comprises excitation unit 22, blocking unit 24, sensor unit 26, and circuitry 110 configured, inter alia, to drive the excitation unit, the blocking unit, and the sensor unit.

System 100 comprises an implant 102 that comprises excitation unit 22, blocking unit 24, and sensor unit 26, and similarly to implant 82, circuitry 110 is implant circuitry.

However, whereas in system 80, power is provided by an extracorporeal controller that transmits the power wirelessly to an antenna of the implant, in system 100 implant 102 comprises a battery 106. Typically, implant 102 comprises a housing 104 that houses units 22, 24 and 26, circuitry 110 and battery 106. Housing 104 is typically elongate. Typically, implant 102 is implanted in the vicinity (e.g., within 10 mm, such as within 7 mm) of nerve 10, e.g., such that a longitudinal axis of the implant is aligned with the nerve. Implant 102 is implanted such that unit 26 is afferent to unit 24, and unit 24 is afferent to unit 22. Typically, implant 102 is implanted by injection.

Therefore, for some applications of the invention, system 100 is similar to system 80, except that power is provided by a battery within the implant, rather than being wirelessly received from an extracorporeal controller. It is to be noted that despite this distinction, implant 102 (e.g., battery 106 thereof) may be wirelessly rechargeable.

The operation of system 100 (as well as that of systems 40, 60 and 80) will be described hereinbelow (e.g., with reference to FIGS. 5-10).

Reference is again made to FIGS. 1-4. Implants 42, 44, 46, 62 and 82 typically comprise no non-transient power storage element (e.g., battery), although they may comprise capacitors. Similarly, implants 42, 44, 46 and 62 typically comprise only simple circuitry that, in the absence of the extracorporeal controller, is not capable of performing the operations described hereinbelow. Therefore, the extracorporeal controllers described hereinabove are typically present during real-time operation of their respective implant(s). That is, the powering and/or operation of the implant(s) is typically performed by the extracorporeal controller in real-time. Typically, the extracorporeal controllers are attachable to the body of the subject, e.g., using a strap 21, and are sufficiently small and light to be worn for a large proportion of the day.

Reference is made to FIGS. 5-10, which are schematic illustrations illustrating the operation of systems 40, 60, 80 and 100, in accordance with some applications of the invention.

Figure 5:
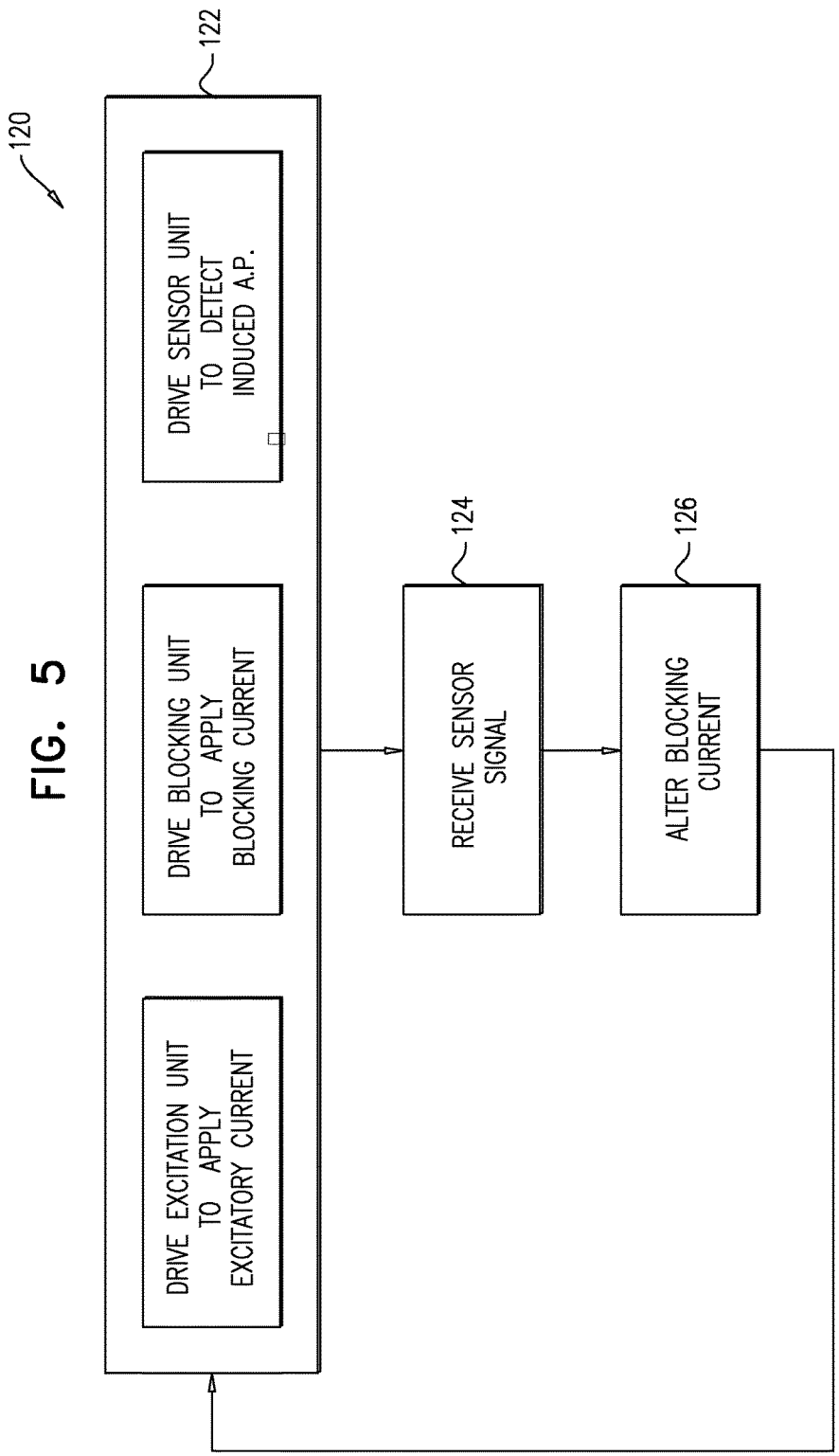

FIG. 5 is a flow diagram of at least some steps of a calibration routine 120 that is performed by the circuitry of systems 40, 60, 80 and 100, in accordance with some applications of the invention. As described hereinabove, the circuitry of each system is configured (i) to drive the excitation unit, the blocking unit, and the sensor unit (step 122), (ii) to receive the sensor signal (step 124), and (iii) in response to the sensor signal, to alter a parameter of (i.e., to calibrate) the blocking current (step 126). The driving of the excitation, blocking and sensor units are shown within a single step 122 because, although (as described with reference to FIGS. 6-9) during routine operation the blocking unit is typically "on" also at times when the excitation and sensor units are "off", during the calibration routine all three units are driven at the same time (e.g., within 10 ms, such as within 5 ms of each other).

FIGS. 6-10 are schematic graphs that illustrate temporal relationships between the driving of the blocking, excitation, and sensor units, according to various applications of the invention. That is, FIGS. 6-10 illustrate, according to various applications of the invention, temporal relationships between the calibration routine and the treatment mode.

In FIGS. 6-9, coincident driving of the blocking, excitation and sensor units is performed as part of the running of a calibration routine. As described hereinabove, the primary function of the systems described herein is typically blocking of undesired action potentials by the blocking unit. Therefore, during routine operation, the blocking unit is typically "on" also at times when the excitation and sensor units are "off" (even, for example, minutes, hours, or days after the excitation and sensor units were last "on"). FIG. 6 illustrates this, showing constant blocking over a period of time (e.g., an hour, a day, or a week), with periodic calibrations (e.g., every few (e.g., 10) minutes, every hour, or every day). However, as illustrated by FIG. 7, blocking need not always be constant, and periodic cessations in blocking may be provided. FIG. 7 also illustrates that for some such applications, multiple calibrations are performed during the course of each continuous blocking period. FIG. 8 shows that for some applications a single calibration is performed during the course of (e.g., at the start of, in the middle of, or at the end of) each blocking period. FIG. 9 shows that for some applications a calibration is not performed during the course of each blocking period, and that one or more calibration-free blocking periods may be provided between blocking periods in which calibration is performed.

Alternatively or additionally, an initial calibration is performed at the start of treatment (e.g., soon after implantation), e.g., initiated by the physician or other medical practitioner.

As described hereinabove, during the calibration routine the blocking, excitation and sensor units are driven at the same time, so as to detect induced action potentials that aren't successfully blocked by the blocking unit. For some applications, a self-checking step is performed (e.g., as part of the calibration routine, or independently of the calibration routine), so as to ensure that a lack of detected induced action potentials (or a low magnitude of the action potentials) is in fact due to successful blocking, rather than to ineffective induction or detection of action potentials (i.e., ineffective performance of the excitation or sensor unit). In such a self-checking step, both the excitation and sensor units are driven, but the blocking unit is not.

FIG. 10 illustrates an example of such a self-checking step. The excitation and sensor units are switched on just prior to the (re)commencement of blocking, such that for a brief period 140 (e.g., 100 ms-10 s, e.g., 100 ms-5 s, such as 100 ms-2 s) any induced action potentials may continue unimpeded to the sensor unit. In response to detecting action potentials during period 140, the sensor unit provides a sensor signal that conveys information about the detected action potentials (e.g., their magnitude and/or frequency), and the circuitry receives and responds to the sensor signal. For some applications, the brevity of period 140 is important, because such induced action potentials may be experienced by the subject as discomfort, paresthesia, or pain (e.g., similarly to the way that the undesired endogenous action potentials are experienced).

For some applications, in response to the sensor signal from period 140, circuitry of the system alters a parameter of (e.g., reconfigures) the excitatory current and/or reconfigures the sensor unit (e.g., a sensitivity thereof).

For some applications, the circuitry of the system compares the action potentials detected during period 140 with those detected during a period 142 in which the blocking unit is also driven, and reconfigures the excitatory current, sensor unit and/or blocking current in response to this comparison.

For some applications, if the detected action potentials of period 140 are insufficient (e.g., of insufficient magnitude), this is indicated by the extracorporeal control unit, and the implant may be repositioned or removed.

For some applications, in response to the sensor signal from period 140, circuitry of the system alters a parameter of (e.g., reconfigures) the blocking current.

Self-checking may be performed (e.g., period 140 may be provided) once (e.g., at around the time of implantation, such as by the physician), occasionally (e.g., during a routine "service" of the system), regularly (e.g., once per day), or often (e.g., before each calibration routine, e.g., automatically). Self-checking may be performed immediately before or after a calibration routine (e.g., period 140 may be provided immediately before or after period 142), as shown in FIG. 10, or may be performed separately.

Reference is now made to FIGS. 11-12, which are schematic illustrations of a system 160 for use with a nerve of a subject, and operation of the system, in accordance with some applications of the invention. System 160 is typically similar to system 60, except where noted. System 160 comprises excitation unit 22, blocking unit 24, and circuitry 170 configured, inter alia, to drive the excitation unit and the blocking unit.

System 160 comprises an implant 162 that comprises excitation unit 22 and blocking unit 24, as well as an intracorporeal antenna 28 (labeled 28f). Typically, implant 162 comprises a housing 164 that houses units 22 and 24, and antenna 28f. Housing 164 is typically elongate. Typically, implant 162 is implanted in the vicinity (e.g., within 10 mm, such as within 7 mm) of nerve 10, e.g., such that a longitudinal axis of the implant is aligned with the nerve. Implant 162 is implanted such that unit 24 is afferent to unit 22. Typically, implant 162 is implanted by injection.

System 160 further comprises an extracorporeal controller 168 that comprises circuitry 170, as well as extracorporeal antenna 32 and battery 34 that powers the circuitry. Circuitry 170 is configured to wirelessly drive (e.g., to wirelessly power and operate) excitation unit 22 and blocking unit 24, via antenna 32 and antenna 28f. Units 22 and 24 are independently addressable by extracorporeal controller 168 (e.g., by circuitry 170 thereof). For example, a code may be modulated onto the wireless power signal, and implant 162 may comprise implant circuitry 166 (e.g., comprising a switch), which directs the received power to the appropriate unit in response to the code. Alternatively, implant 162 may comprise a separate antenna for each of units 22 and 24, and the wireless power signal is configured to have a particular characteristic (e.g., frequency) that only a particular antenna is configured to receive.

Therefore, for some applications of the invention, system 160 is similar to system 60, except that it lacks a sensor unit. Controller 168 comprises an interface 172 that typically comprises a display and/or an input such as buttons or a dial. The calibration of the blocking current of system 160 is performed in response to user operation of interface 172. The calibration of the blocking current of system 160 is typically performed manually. Excitation unit 22 is driven by controller 168 in response to user operation of interface 172 (e.g., initiation of the calibration routine). The afferent action potentials induced by excitation unit 22 are experienced by the subject, e.g., as a sensation, discomfort, paresthesia, or pain. While excitation unit continues to initiate these action potentials, blocking unit 24 is driven by controller 168. (The driving of blocking unit 24 may start simultaneously with the driving of excitation unit 22, may start automatically after a delay, or may start upon receiving a separate instruction from user operation of interface 172.) By operating interface 172, the user (e.g., the subject or the physician) manually causes circuitry 170 to wirelessly calibrate the blocking current until the induced action potentials are experienced less strongly (e.g., until they are no longer experienced).

It is to be noted that the scope of the invention includes a system similar to system 160, but with circuitry 170 replaced with implant circuitry (e.g., similar to implant circuitry 90 of system 80, mutatis mutandis). Similarly, the scope of the invention includes a similar system without an extracorporeal controller, and instead with the implant comprising a battery (e.g., similar to system 100, mutatis mutandis).

For some applications, and as shown, excitation unit 22 is disposed within a first half of elongate housing 164 (e.g., a half that includes a first end of the housing), and blocking unit 24 is disposed within a second half of the housing (e.g., a half that includes a second, opposite end of the housing). Therefore, for some applications, an implant is provided that has a longitudinal axis, is injectable into the subject along the longitudinal axis, and comprises:

(i) an elongate housing having a first half including a first end, and a second half including a second end;

(ii) at least one paresthesia-inducing electrode (i.e., of excitation unit 22) disposed on a first site of the housing within the first half;

(ii) at least one blocking electrode (i.e., of blocking unit 24) disposed on a second site of the housing within the second half; and (iv) circuitry (which may be circuitry 170, or may be implant circuitry), having:

a first mode (e.g., for the calibration routine) in which the circuitry simultaneously drives (a) the at least one paresthesia-inducing electrode to apply a paresthesia-inducing current having a frequency of 2-400 Hz, and (b) the at least one blocking electrode to apply a blocking current having a frequency of 1-20 kHz, and a second mode (e.g., a treatment mode) in which the circuitry (a) drives the at least one blocking electrode to apply the blocking current, but (b) does not drive the at least one paresthesia-inducing electrode to apply the paresthesia-inducing current.

FIG. 12 is a flow diagram of at least some steps of a calibration routine 180 that is performed on system 160, in accordance with some applications of the invention. As described hereinabove, circuitry 170 of system 160 is configured (i) to drive excitation unit 22 and blocking unit 24 (step 182), (ii) to receive input via user operation of user interface 172 (step 184), and (iii) in response to the input, to alter a parameter of (i.e., to calibrate) the blocking current (step 186). The driving of the excitation and blocking units are shown within a single step 182 because, although (as described hereinabove) during routine operation the blocking unit is typically "on" also at times when the excitation unit is "off", during the calibration routine both units are driven at the same time (e.g., within 10 ms, such as within 5 ms of each other).

The timing of the calibration routine of system 160, with respect to its treatment mode, may follow one or more of those described for systems 40, 60, 80 and 100 (e.g., with reference to FIGS. 6-10), mutatis mutandis. Similarly, self-checking may be performed on system 160, in which excitation unit 22 but not blocking unit 24 is driven.

Reference is again made to FIGS. 1, 2, 5-10, 11 and 12. It is to be noted that, for each of systems 40, 60 and 160, the system comprises:

(i) implantable excitation unit 22, configured to induce action potentials in the nerve by applying an excitatory current to the nerve;

(ii) implantable blocking unit 24, configured to block the induced action potentials from propagating along the nerve by applying a blocking current to the nerve; and (iii) an extracorporeal controller (e.g., controller 48, 68 or 168), comprising at least one antenna, circuitry (e.g., circuitry 50, 70 or 170).

As described hereinabove, the primary function of each system is blocking of undesirable endogenous action potentials. Consequently, in a first mode (e.g., a treatment mode) of the system (e.g., of the extracorporeal controller), the blocking current but not the excitatory current is driven. Typically, at least 90 percent of the time that the blocking current is driven, the excitatory current is not driven. In a second mode (e.g., a calibration mode) of the system (e.g., of the extracorporeal controller), both the blocking and excitatory currents are driven, e.g., for the calibration routine. Typically, only during self-checking is the excitatory current driven in the absence of the blocking current. Typically, even for applications in which self-checking is used, more than 30 percent of the time that the excitatory current is driven, the blocking current is also driven.

The circuitry (e.g., circuitry 50, 70 or 170) is configured:

(i) to wirelessly drive the excitation unit to apply the excitatory current, (ii) in a first mode (e.g., the treatment mode) of the extracorporeal controller, to wirelessly drive the blocking unit to apply the blocking current while not driving the excitation unit to apply the excitatory current, (iii) in a second mode of the extracorporeal controller (e.g., the calibration mode), to wirelessly drive the blocking unit to apply the blocking current while driving the excitation unit to apply the excitatory current, and (iv) to wirelessly alter a parameter of the blocking current, based on sensing performed while the extracorporeal controller is in the second mode. As described hereinabove, for systems 40 and 60, this sensing is performed by sensor unit 26, and the circuitry automatically receives and responds to it (i.e., to the sensor signal). For system 160, this sensing is performed by the subject, who responsively manually operates interface 172, to which the circuitry responds.

For some applications, the switching between the first and second modes is performed automatically by the circuitry (e.g., according to a calibration routine). That is, for some applications the circuitry automatically periodically switches the extracorporeal controller into the second mode for the calibration routine, and subsequently switches it back into the first mode. For some applications, the circuitry is configured to switch the extracorporeal controller between the first and second modes in response to user operation of the user interface (i.e., calibration is initiated and/or performed manually by the subject or a physician.

During self-checking (e.g., during period 140), the extracorporeal controller may be considered to be in a third mode in which the excitation unit but not the blocking unit is driven.

Reference is again made to FIGS. 1-12. The primary function of each system is blocking of undesirable endogenous action potentials. Consequently, in a first mode (e.g., a treatment mode) of the system, the blocking current but not the excitatory current is driven. Typically, at least 90 percent of the time that the blocking current is driven, the excitatory current is not driven. In a second mode (e.g., a calibration mode) of the system, both the blocking and excitatory currents are driven, e.g., for the calibration routine. Typically, only during self-checking is the excitatory current driven in the absence of the blocking current. Typically, even for applications in which self-checking is used, more than 30 percent of the time that the excitatory current is driven, the blocking current is also driven. The driving of blocking unit 24 (whether wirelessly by extracorporeal circuitry or wiredly by implant circuitry), is achieved by the circuitry providing a blocking-command signal (which typically powers the blocking unit). This signal has an energy consumption, and the calibration routine of each system is configured to reduce this energy consumption as far as possible. At least because the excitatory current is driven much less (e.g., for shorter periods and/or less frequently) than the blocking current, the extra energy consumption required for the calibration routine is more than offset by the reduction in the energy consumption of the blocking-command signal.

Reference is again made to FIGS. 1-12. The implants described herein are typically injectable, and to facilitate this are typically dimensioned to fit longitudinally through an 8-16 gauge needle (e.g., an 11-14 gauge needle).

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus, for use with a nerve of a subject, the apparatus comprising:

an implantable excitation unit, including an excitation-unit electrode, and configured to induce action potentials in the nerve by driving the excitation-unit electrode to apply an excitatory current to the nerve;

an implantable blocking unit, including a blocking-unit electrode, and configured to block the induced action potentials from propagating along the nerve by driving the blocking-unit electrode to apply a blocking current to the nerve;

an implantable sensor unit:
configured to detect the induced action potentials in the nerve,
including a sensor unit antenna, and
configured to provide, via the sensor unit antenna, and in response to detecting the induced action potentials in the nerve, a sensor signal that conveys information about the detected induced action potentials; and an extracorporeal controller, programmed with a first mode and a second mode, and comprising (i) at least one controller antenna, and (ii) circuitry configured to, via the at least one controller antenna:

wirelessly drive the excitation unit to apply the excitatory current, in the first mode of the extracorporeal controller, wirelessly drive the blocking unit to apply the blocking current while not driving the excitation unit to apply the excitatory current, and in the second mode of the extracorporeal controller, wirelessly drive the blocking unit to apply the blocking current while driving the excitation unit to apply the excitatory current, wherein the circuitry is programmed with a calibration routine, and is configured to automatically periodically run the calibration routine, the calibration routine comprising:
(a) switching the extracorporeal controller into the second mode,
(b) via the at least one controller antenna, wirelessly receiving the sensor signal, the sensor signal conveying information about induced action potentials detected while the extracorporeal controller is in the second mode,
(c) in response to the sensor signal received in step (b) of the calibration routine, wirelessly altering a parameter of the blocking current, and
(d) switching the extracorporeal controller into the first mode.

2. The apparatus according to claim 1, wherein the extracorporeal controller is programmed with a third mode, in which the circuitry is configured to wirelessly drive the excitation unit to apply the excitatory current while not driving the blocking unit to apply the blocking current.

3. The apparatus according to claim 1, wherein the excitatory current has a frequency of 2-400 Hz, and the circuitry is configured to wirelessly drive the excitation unit to apply the excitatory current having the frequency of 2-400 Hz.

4. The apparatus according to claim 3, wherein the excitatory current has a frequency of 5-100 Hz, and the circuitry is configured to wirelessly drive the excitation unit to apply the excitatory current having the frequency of 5-100 Hz.

5. The apparatus according to claim 1, wherein the blocking current has a frequency of 1-20 kHz, and the circuitry is configured to wirelessly drive the blocking unit to apply the blocking current having the frequency of 1-20 kHz.

6. The apparatus according to claim 5, wherein the blocking current has a frequency of 3-10 kHz, and the circuitry is configured to wirelessly drive the blocking unit to apply the blocking current having the frequency of 3-10 kHz.

7. The apparatus according to claim 1, further comprising an implantable device that comprises a housing that houses the excitation unit, the blocking unit, and the sensor unit.

8. The apparatus according to claim 1, wherein the extracorporeal controller is programmed with a third mode, in which the circuitry is configured to wirelessly drive the excitation unit to apply the excitatory current while not driving the excitation unit to apply the blocking current, and wherein the calibration routine further comprises, prior to step (a)
(i) switching the extracorporeal controller into the third mode, and
(ii) receiving the sensor signal, the sensor signal conveying information about induced action potentials detected while the extracorporeal controller is in the third mode.

9. The apparatus according to claim 8, wherein step (c) of the calibration routine comprises altering the parameter of the blocking current in response to the sensor signal received in step (b) of the calibration routine, and in response to the sensor signal received in step (ii) of the calibration routine.

10. The apparatus according to claim 1, wherein the extracorporeal controller further comprises a user interface, and wherein the circuitry is configured to switch the extracorporeal controller between the first and second modes in response to user operation of the user interface.

* * * * *